US005798257A

United States Patent [19]
Zain et al.

[11] Patent Number: 5,798,257
[45] Date of Patent: Aug. 25, 1998

[54] NUCLEIC ACID ENCODING HUMAN MTS-1 PROTEIN

[75] Inventors: Sayeeda Zain, Pittsford, N.Y.; Eugene Lukanidin, Copenhagen, Denmark

[73] Assignee: Research Corporation Technologies, Inc., Tucson, Ariz.

[21] Appl. No.: 190,560

[22] Filed: Jan. 31, 1994

Related U.S. Application Data

[63] Continuation-in-part of Ser. No. 981,455, Nov. 25, 1992, abandoned, which is a continuation of Ser. No. 550,600, Jul. 9, 1990, abandoned.

[51] Int. Cl.$^6$ .......................... C12N 15/12; C12N 15/81; C12N 15/85
[52] U.S. Cl. .................... 435/252.3; 435/320.1; 435/325; 435/348; 435/419; 435/254.2; 536/23.5
[58] Field of Search .................... 536/23.2, 23.5; 435/240.2, 252.3, 325, 348, 419, 254.2, 320.1; 530/350

[56] References Cited

PUBLICATIONS

Linzer, et al., Proc. Natl. Acad. Sci., 80:4271–4275 (1983).
Suggs et al., PNAS vol. 78, No. 11, pp. 6613–6617, Nov. 1981.
Lukanidin et al., J. Cell Biochem, Suppl. 13 B, Abstract # D 422, p. 66, 1989.
Tulchinsky et al., Gene, vol. 87, pp. 219–223, 1990.
Lukanidin, et al., "Isolation and Characterization of a New Gene for a Ca++ –binding Proteins which is Specifically Expressed in Different Metastatic Cells, " J. Cellular Biochem., Suppl. 13B, p. 66, Abstract D 422 (1989).
Baudier, et al., "Ions Binding to S100 Proteins," J. Biol. Chem., 261(18): 8204–8212 (Jun. 25, 1986).
Barraclough, et al., "The Identification of a Normal Rat Gene Located Close to the Gene for the Potential Myoepithelial Cell Calcium–binding Protein, p9Ka," J. Biol. Chem., 263(29): 14597–14600 (Oct. 15, 1988).
Barraclough, et al., "Calcium–ion Binding by the Potential Calcium–ion binding Protein, p9Ka," Biochem. and Biophys. Res. Comm., 169(2): 660–666 (Jun. 15, 1990).
Barraclough, et al., "Molecular Cloning and Sequence of the Gene for p9Ka, a Cultured Myoepithelial Cell Protein with Strong Homology to S–100, a Calcium–binding Protein," J. Mol. Biol., 198(1): 13–20 (Nov. 5, 1987).
Jackson–Grusby, et al., "A Growth Related mRNA in Cultured Mouse Cells Encodes a Placental Calcium Binding Protein," Nuc. Acids Res., 15(16): 6677–6690 (Aug. 25, 1987).
Goto, et al., "Cloning of the Sequences Expressed Abundantly in Established Cell Lines: Identification of a cDNA Clone Highly Homologous to S–100, a Calcium–binding Protein," J. Biochem., 103(1): 48–53 (Jan. 1988).
Masiakowski, et al., "Nerve Growth Factor Induces the Genes for Two Proteins Related to a Family of Calcium–binding Proteins in PC12 Cells," Proc. Nat'l Acad. Sci. USA, 85(4): 1277–1281 (Feb. 1988).
Tulchinsky, et al., "Structure of Gene mts–1, transcribed in Metastatic Mouse Tumor Cells," Gene, 87: 219–223 (1990).
Linzer, et al., "Growth–related Changes in Specific mRNAs of Cultured Mouse Cells," Proc. Nat'l Acad. Sci, USA, 80(14): 4271–4275 (Jul. 1983).
Ebralidze, et al., "Isolation and Characterization of a Gene Specifically Expressed in Different Metastatic Cells and Whose Deduced Gene Product has a High Degree of Homology to a $Ca^{2+}$–binding Protein Family," Genes & Devel., 3: 1086–1093 (1989).

Primary Examiner—Keith D. Hendricks
Attorney, Agent, or Firm—Scully, Scott, Murphy & Presser

[57] ABSTRACT

The present invention is directed towards the diagnosis of malignant cancer by detection of the mts-1 mRNA or the mts-1 protein, encoded by the mts-1 gene. The present invention contemplates the use of recombinant mts-1 DNA and antibodies directed against the mts-1 protein to diagnose the metastatic potential of several types of tumor cells, including, for example, thyroid, epithelial, lung, liver and kidney tumor cells. The present invention is also directed to mammalian cell lines and tumors with high and low metastatic potential which have been developed to serve as useful model systems for in vitro and in vivo anti-metastasis drug screening.

20 Claims, 25 Drawing Sheets

(16 of 29 Drawing(s) in Color)

Human mts-1 Nucleotide Sequence

ATG-GCG-TGC-CCT-CTG-GAG-AAG-GCC-CTG-GAT-GTG-ATG-GTG-TCC-ACC-

TTC-CAC-AAG-TAC-TCG-GGC-AAA-GAG-GGT-GAC-AAG-TTC-AAG-CTC-AAC-

AAG-TCA-GAG-CTA-AAG-GAG-CTG-CTG-ACC-CGG-GAG-CTG-CCC-AGC-TTC-

TTG-GGG-AAA-AGG-ACA-GAT-GAA-GCT-GCT-TTC-CAG-AAG-CTG-ATG-AGC-

AAC-TTG-GAC-AGC-AAC-AGG-GAC-AAC-GAG-GTG-GAC-TTC-CAA-GAG-TAC-

TGT-GTC-TTC-CTG-TCC-TGC-ATC-GCC-ATG-ATG-TGT-AAC-GAA-TTC-TTT-

GAA-GGC-TTC-CCA-GAT-AAG-CAG-CCC-AGG-AAG-AAA

FIG.1

Human mts-1 Amino Acid Sequence 1                                                                               14

Met-Ala-Cys-Pro-Leu-Glu-Lys-Ala-Leu-Asp-Val-Met-Val-Ser-
Thr-Phe-His-Lys-Tyr-Ser-Gly-Lys-Glu-Gly-Asp-Lys-Phe-Lys-
Leu-Asn-Lys-Ser-Glu-Leu-Lys-Glu-Leu-Leu-Thr-Arg-Glu-Leu-
Pro-Ser-Phe-Leu-Gly-Lys-Arg-Thr-Asp-Glu-Ala-Ala-Phe-Gln-
Lys-Leu-Met-Ser-Asn-Leu-Asp-Ser-Asn-Arg-Asp-Asn-Glu-Val-
Asp-Phe-Gln-Glu-Tyr-Cys-Val-Phe-Leu-Ser-Cys-Ile-Ala-Met-
Met-Cys-Asn-Glu-Phe-Phe-Glu-Gly-Phe-Pro-Asp-Lys-Gln-Pro-
Arg-Lys-Lys

FIG. 2

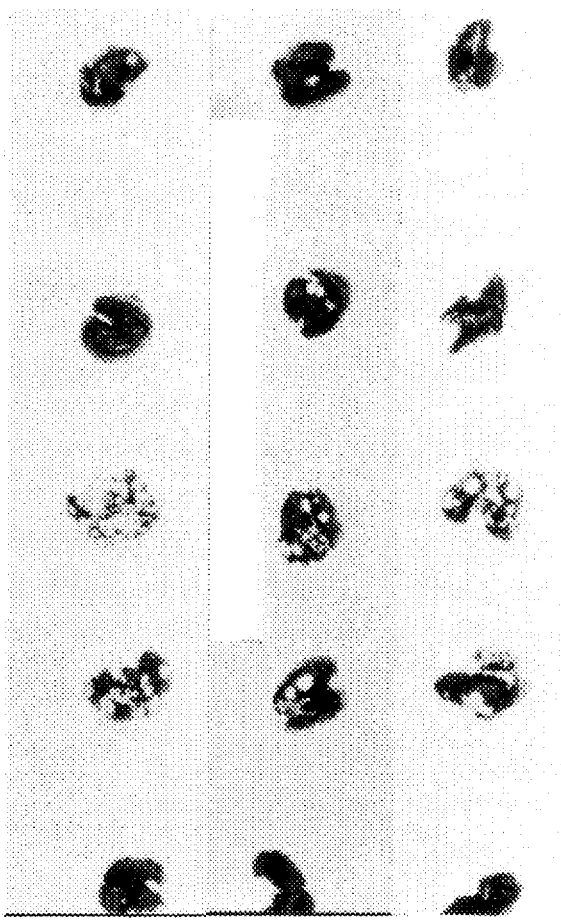

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 303 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
ATGGCGTGCC CTCTGGAGAA GGCCCTGGAT GTGATGGTGT CCACCTTCCA CAAGTACTCG      60
GGCAAAGAGG GTGACAAGTT CAAGCTCAAC AAGTCAGAGC TAAAGGAGCT GCTGACCCGG     120
GAGCTGCCCA GCTTCTTGGG GAAAAGGACA GATGAAGCTG CTTTCCAGAA GCTGATGAGC     180
AACTTGGACA GCAACAGGGA CAACGAGGTG GACTTCCAAG AGTACTGTGT CTTCCTGTCC     240
TGCATCGCCA TGATGTGTAA CGAATTCTTT GAAGGCTTCC CAGATAAGCA GCCCAGGAAG     300
AAA                                                                   303
```

( 2 ) INFORMATION FOR SEQ ID NO:2:

( i ) SEQUENCE CHARACTERISTICS:
        ( A ) LENGTH: 101 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Ala Cys Pro Leu Glu Lys Ala Leu Asp Val Met Val Ser Thr Phe
 1               5                  10                  15
His Lys Tyr Ser Gly Lys Glu Gly Asp Lys Phe Lys Leu Asn Lys Ser
            20                  25                  30
Glu Leu Lys Glu Leu Leu Thr Arg Glu Leu Pro Ser Phe Leu Gly Lys
        35                  40                  45
Arg Thr Asp Glu Ala Ala Phe Gln Lys Leu Met Ser Asn Leu Asp Ser
    50                  55                  60
Asn Arg Asp Asn Glu Val Asp Phe Gln Glu Tyr Cys Val Phe Leu Ser
65                  70                  75                  80
Cys Ile Ala Met Met Cys Asn Glu Phe Phe Glu Gly Phe Pro Asp Lys
                85                  90                  95
Gln Pro Arg Lys Lys
            100
```

( 2 ) INFORMATION FOR SEQ ID NO:3:

( i ) SEQUENCE CHARACTERISTICS:
        ( A ) LENGTH: 579 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

```
GGCAGTTGAG GCAGGAGACA TCAAGAGAGT ATTTGTGCCC TCCTCGGGTT TTACCTTCCA      60
```

| | | | | | |
|---|---|---|---|---|---|
|GCCGAGATTC|TTCCCCTCTC|TACAACCCTC|TCTCCTCAGC|GCTTCTTCTT|TCTTGGTTTG 120|
|ATCCTGACTG|CTGTCATGGC|GTGCCCTCTG|GAGAAGGCCC|TGGATGTGAT|GGTGTCCACC 180|
|TTCCACAAGT|ACTCGGGCAA|AGAGGGTGAC|AAGTTCAAGC|TCAACAAGTC|AGAACTAAAG 240|
|GAGCTGCTGA|CCCGGGAGCT|GCCCAGCTTC|TTGGGGAAAA|GGACAGATGA|AGCTGCTTTC 300|
|CAGAAGCTGA|TGAGCAACTT|GGACAGCAAC|AGGGACAACG|AGGTGGACTT|CCAAGAGTAC 360|
|TGTGTCTTCC|TGTCCTGCAT|CGCCATGATG|TGTAACGAAT|TCTTTGAAGG|CTTCCCAGAT 420|
|AAGCAGCCCA|GGAAGAAATG|AAAACTCCTC|TGATGTGGTT|GGGGGGTCTG|CCAGCTGGGG 480|
|CCCTCCCTGT|CGCCAGTGGG|CACTTTTTTT|TTTCCACCCT|GGCTCCTTCA|GACACGTGCT 540|
|TGATGCTGAG|CAAGTTCAAT|AAAGATTCTT|GGAAGTTTA| | 579|

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:4:

Ala Cys Pro Leu Glu Lys Ala Leu Asp Val
    1               5                   10

( 2 ) INFORMATION FOR SEQ ID NO:5:

( i ) SEQUENCE CHARACTERISTICS:
        ( A ) LENGTH: 16 amino acids
        ( B ) TYPE: amino acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:5:

Lys Glu Gly Asp Lys Phe Lys Leu Asn Lys Ser Glu Leu Lys Glu Leu
    1               5                   10                  15

( 2 ) INFORMATION FOR SEQ ID NO:6:

( i ) SEQUENCE CHARACTERISTICS:
        ( A ) LENGTH: 13 amino acids
        ( B ) TYPE: amino acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

Leu Pro Ser Phe Leu Gly Lys Arg Thr Asp Glu Ala Ala
    1               5                   10

( 2 ) INFORMATION FOR SEQ ID NO:7:

( i ) SEQUENCE CHARACTERISTICS:
        ( A ) LENGTH: 15 amino acids
        ( B ) TYPE: amino acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:7:

| Asn | Glu | Phe | Phe | Glu | Gly | Phe | Pro | Asp | Lys | Gln | Pro | Arg | Lys | Lys |
|-----|-----|-----|-----|-----|-----|-----|-----|-----|-----|-----|-----|-----|-----|-----|
| 1   |     |     |     | 5   |     |     |     |     | 10  |     |     |     |     | 15  |

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

ATGGCGTGCC CTCTGGAGAA G       21

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

TTTCTTCCTG GGCTGCTTAT G       21

NUCLEIC ACID ENCODING HUMAN MTS-1 PROTEIN

The present application is a continuation-in-part of U.S. application Ser. No. 07/981,455, filed Nov. 25, 1992, now abandoned, which is a continuation of U.S. application Ser. No. 07/550,600, filed Jul. 9, 1990, now abandoned.

FIELD OF THE INVENTION

The present invention is directed towards the diagnosis of malignant cancer by detection of the mts-1 mRNA or the mts-1 protein encoded by the mts-1 gene. The present invention contemplates the use of recombinant mts-1 DNA and antibodies directed against the mts-1 protein to diagnose the metastatic potential of several types of tumor cells, including, for example, thyroid, epithelial, lung, liver, kidney, breast, lymphoid, hematopoietic, pancreatic, endometrial, ovarian, cervical, skin, colon and similar tumor cells. The present invention is also directed to mammalian cell lines and tumors with high and low metastatic potential which have been developed to serve as useful model systems for in vitro and in vivo anti-metastasis drug screening.

BACKGROUND OF THE INVENTION

Malignant cancer tumors shed cells which migrate to new tissues and create secondary tumors; a benign tumor does not generate secondary tumors. The process of generating secondary tumors is called metastasis and is a complex process in which tumor cells colonize sites distant from the primary tumor. Tumor metastasis remains the major cause of morbidity and death for patients with cancer. One of the greatest challenges in cancer research is to understand the basis of metastasis, i.e., what controls the spread of tumor cells through the blood and lymphatic systems and what allows tumor cells to populate and flourish in new locations.

The metastatic process appears to be sequential and selective, and is controlled by a series of steps since metastatic tumor cells: (a) are mobile and can disseminate from the original tumor; (b) are capable of invading the cellular matrix and penetrating through blood vessels; (c) possess immunological markers, which allow them to survive passage through the blood stream, where they must avoid the immunologically active cytotoxic "T" lymphocytes; and (d) have the ability to find a favorable location to transplant themselves and successfully survive and grow.

Understanding the underlying molecular mechanisms in metastasis is the key to understanding cancer biology and its therapy. In clinical lesions, malignant tumors contain a heterogeneous population of cells, exhibiting a variety of biological characteristics, e.g., differential growth rates, cell surface structures, invasive capacities and sensitivity to various cytotoxic drugs. Researchers can take advantage of tumor heterogeneity factors, by identifying specific cell produced markers, which are unique for metastasis, to develop therapeutic regiments which do not rely only on surgical resection.

At this time it is not known whether the metastatic phenotype is under the regulation of a single or multiple gene(s), and whether these genes are independent or inter-related. However, a number of genes have become correlated with the formation and metastasis of tumors. For example, several normal cellular genes become oncogenes by incorporation into a retroviral genome. Due to the juxtaposition of new promoter elements, such incorporation frequently allows a potential oncogene to be expressed in inappropriate tissues or at higher levels than it normally would be expressed. It appears from work with tumorigenic retroviruses as well as other systems that misexpression of many cellular proteins, particularly those involved in the regulation of the cell cycle, cell mobility, or cell-cell interaction may lead to a cancerous phenotype.

The present invention discloses the human mts-1 gene and diagnosis of metastatic cancer by use of either antibodies directed against the mts-1 protein or mts-1 nucleic acid probes directed against mts-1 mRNA.

The mouse and rat mts-1 genes have been previously isolated under different names (i.e., 18A2, Linzer, et al., Proc. Natl. Acad. Sci. U.S.A. 80:4271–4275, 1983; and p9Ka, Barraclough et al., J. Mol. Biol. 198:13–20, 1987) but no function or correlation of the mts-1 gene in metastatic cancer has been established prior to the present invention. Previous work has indicated that the protein now identified as the mts-1 protein is a calcium binding protein with homology to other calcium binding proteins such as, for example, the S-100 calcium protein, which are thought to have a role in cell growth (Linzer et al. supra; Jackson-Grusby et al., Nuc. Acids Res. 15:6677–6690, 1987; Goto et al., J. Biochem. 103:48–53, 1988). Other researchers suggest a role for p9Ka, later found to be identical to mts-1, in myoepithelial cell differentiation (Barraclough, et al., supra).

As determined uniquely by the present invention, the mammalian mts-1 gene is expressed at 10– 100 fold higher levels in metastatic cells compared to non-metastatic cells and normal cells. Only a few types of normal cells, including lymphocytes and trophoblasts, express mts-1. Hence, the present invention demonstrates a surprising new property of mts-1: the misexpression of mts-1 within a cell or tissue is diagnostic of malignant cancer.

SUMMARY OF THE INVENTION

The present invention is directed towards the diagnosis of metastatic cancer using an mts-1 nucleic acid or antibodies directed against the mts-1 protein. The present invention is also directed to isolated and purified mts-1 nucleic acids available for diagnostic tests and antibodies directed against the mammalian mts-1 proteins.

One aspect of the present invention is directed to a method for diagnosing metastatic cancer by contacting serum from an individual to be tested for such cancer with an antibody reactive with a mammalian mts-1 protein or an antigenic fragment thereof, for a time and under conditions sufficient to form an antigen-antibody complex, and detecting the antigen-antibody complex.

Another aspect of the present invention provides an isolated, recombinant nucleic acid encoding a human mts-1 gene or a fragment thereof, and replicable DNA sequences encoding an mts-1 polypeptide which express high levels of the mts-1 polypeptide. Isolated antisense mts-1 nucleic acids and expression vectors therefor are also contemplated by the present invention. Human mts-1 nucleic acids are preferred.

A further aspect of this invention is directed to isolated transformed host cells, such as prokaryotic microorganisms, yeast, insect cells and eukaryotic cells, containing mts-1 nucleic acids and replicable vectors containing DNA sequences encoding the mts-1 polypeptide.

A still further aspect of this invention provides isolated homogeneous mammalian mts-1 polypeptides and pharmaceutical compositions including such a mts-1 polypeptide or protein. Human mts-1 polypeptides are preferred.

Another aspect of this invention provides antibodies directed against an mts-1 polypeptide or any peptide, fragment or derivative of the mts-1 protein.

A further aspect of this invention is directed towards treatment of cancer by administering reagents, such as for example, anti-mts-1 antibodies capable of binding the mts-1 protein and antisense mts-1 nucleic acids capable of binding mts-1 sense mRNA.

Yet another aspect of the present invention provides an animal model system of the metastatic process, including several eukaryotic cell lines and tumors expressing different levels of mts-1, which are derived from mouse and rat carcinomas. These cell lines and tumors may be re-introduced into mice or rats to produce primary tumors which metastasize to the lung, liver and kidneys with a characteristic frequency. Therefore, the present invention also provides a well controlled animal model system for testing pharmaceutical compositions suspected to have therapeutic utility for the treatment of metastatic cancer.

BRIEF DESCRIPTION OF THE DRAWINGS

This application contains color drawings.

FIG. 1 depicts the nucleotide sequence of the coding region of the human mts-1 gene.

FIG. 2 depicts the amino acid sequence of the human mts-1 protein.

FIG. 9a depicts the lungs from 3 mice injected subcutaneously with 1×10$^6$ CSML-0 cells. Lungs were removed 4–6 weeks after injection and then injected with India ink. Dark areas indicate normal tissues; white areas are tumors.

FIG. 9b depicts the lungs from 3 mice injected intravenously with 1×10$^4$ CSML-0 cells. Lungs were removed 15 days after injection and then injected with India ink. Dark areas indicate normal tissues; white areas are tumors.

FIG. 9c depicts the lungs from 3 mice injected intravenously with 1×10$^4$ CSML-100 cells. Lungs were removed 15 days after injection and then injected with India ink. Dark areas indicate normal tissues; white areas are tumors.

FIG. 9d depicts the lungs from 3 mice injected subcutaneously with 1×10$^6$ CSML-100 cells. Lungs were removed 4–6 weeks after injection and then injected with India ink. Dark areas indicate normal tissues; white areas are tumors.

FIG. 9e depicts the lungs from 3 mice injected with 0.1 ml serum-free media. Lungs were removed 6–8 weeks after injection and then injected with India ink. Dark areas indicate normal tissues; white areas are tumors.

DETAILED DESCRIPTION OF THE INVENTION

Figure 3:
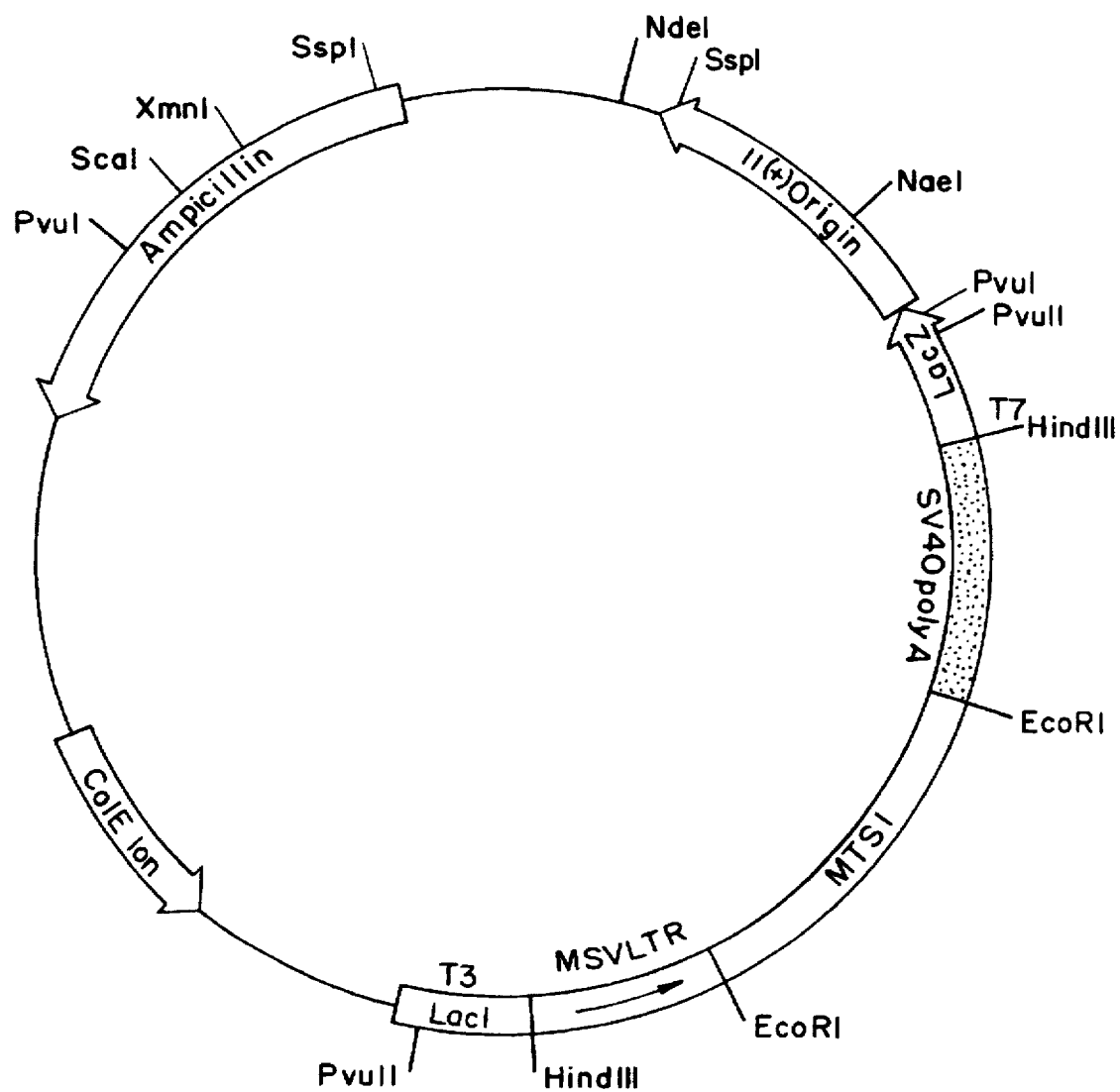
FIG. 3 depicts the circular, expression plasmid pEMS-Vscribe2 containing the complete coding region of mts-1 under the control of the murine sarcoma virus promoter (MSV LTR).

The present invention provides a new method for diagnosing metastatic cancer and for distinguishing metastatic tumors from benign tumors. In particular, the present invention demonstrates a heretofore unknown property of a mammalian gene, called mts-1, whose expression is about 10 to about 100 fold higher in metastatic tumor cells, for example, of the lung, liver, kidney, mammary gland, epithelial, thyroid, leukemic, pancreatic, endometrial, ovarian, cervical, skin, colon or lymphoid tissue than in benign tumor cells or the corresponding normal cells. According to the present invention metastatic cancer of these and other tissues can be detected in patient's serum by a simple immunoassay. Moreover, metastatic cancer can also be diagnosed in tissue biopsies by the present immunoassays or by in situ hybridization assays.

Metastasis is the formation of secondary tumors by cells derived from a primary tumor. The metastatic process involves mobilization and migration of primary tumor cells from the site of the primary tumor into new tissues where the primary tumor cells induce the formation of secondary (metastatic) tumors. In accordance with the present inventive discovery, the increased expression of the mts-1 gene in a cell or tissue is strongly indicative of metastatic potential. The present invention utilizes this unexpected and surprising correlation of high mammalian mts-1 gene expression with high metastatic potential to detect or diagnose malignant cancer. Both the mammalian mts-1 nucleic acid and antibodies directed against mammalian mts-1 proteins are contemplated for use in the diagnosis of malignant cancer. The human mts-1 gene, depicted by one of the nucleotide sequences below, has been isolated for the first time in the present invention.

SEQ ID NO:1

ATG—GCG—TGC—CCT—CTG—GAG—AAG—GCC—CTG—GAT—GTG—ATG—GTG—TCC—

ACC—TTC—CAC—AAG—TAC—TCG—GGC—AAA—GAG—GGT—GAC—AAG—TTC—AAG—

CTC—AAC—AAG—TCA—GAG—CTA—AAG—GAG—CTG—CTG—ACC—CGG—GAG—CTG—

CCC—AGC—TTC—TTG—GGG—AAA—AGG—ACA—GAT—GAA—GCT—GCT—TTC—CAG—

AAG—CTG—ATG—AGC—AAC—TTG—GAC—AGC—AAC—AGG—GAC—AAC—GAG—GTG—

GAC—TTC—CAA—GAG—TAC—TGT—GTC—TTC—CTG—TCC—TGC—ATC—GCC—ATG—

ATG—TGT—AAC—GAA—TTC—TTT—GAA—GGC—TTC—CCA—GAT—AAG—CAG—CCC—

AGG—AAG—AAA; or

SEQ ID NO:3

-continued
GGC—AGT—TGA—GGC—AGG—AGA—CAT—CAA—GAG—AGT—ATT—TGT—GCC—

CTC—CTC—GGG—TTT—TAC—CTT—CCA—GCC—GAG—ATT—CTT—CCC—CTC—

TCT—ACA—ACC—CTC—TCT—CCT—CAG—CGC—TTC—TTC—TTT—CTT—GGT—

TTG—ATC—CTG—ACT—GCT—GTC—ATG—GCG—TGC—CCT—CTG—GAG—AAG—

GCC—CTG—GAT—GTG—ATG—GTG—TCC—ACC—TTC—CAC—AAG—TAC—TCG—

GGC—AAA—GAG—GGT—GAC—AAG—TTC—AAG—CTC—AAC—AAG—TCA—GA<u>A</u>—

CTA—AAG—GAG—CTG—CTG—ACC—CGG—GAG—CTG—CCC—AGC—TTC—TTG—

GGG—AAA—AGG—ACA—GAT—GAA—GCT—GCT—TTC—CAG—AAG—CTG—ATG—

AGC—AAC—TTG—GAC—AGC—AAC—AGG—GAC—AAC—GAG—GTG—GAC—TTC—

CAA—GAG—TAC—TGT—GTC—TTC—CTG—TCC—TGC—ATC—GCC—ATG—ATG—

TGT—AAC—GAA—TTC—TTT—GAA—GGC—TTC—CCA—GAT—AAG—CAG—CCC—

AGG—AAG—AAA—<u>TGA—AAA</u>—CTC—CTC—TGA—TGT—GGT—TGG—GGG—GTC—

TGC—CAG—CTG—GGG—CCC—TCC—CTG—TCG—CCA—GTG—GGC—ACT—TTT—

TTT—TTT—CCA—CCC—TGG—CTC—CTT—CAG—ACA—CGT—GCT—TGA—TGC—

TGA—GCA—AGT—TCA—ATA—AAG—ATT—CTT—GGA—AGT—TTA—, wherein SEQ ID NO:3 is different from SEQ ID NO:1 at the underlined positions.

The amino acid sequence of the human mts-1 protein is depicted below (SEQ ID NO:2):

Met—Ala—Cys—Pro—Leu—Glu—Lys—Ala—Leu—Asp—Val—Met—Val—Ser—

Thr—Phe—His—Lys—Tyr—Ser—Gly—Lys—Glu—Gly—Asp—Lys—Phe—Lys—

Leu—Asn—Lys—Ser—Glu—Leu—Lys—Glu—Leu—Leu—Thr—Arg—Glu—Leu—

Pro—Ser—Phe—Leu—Gly—Lys—Arg—Thr—Asp—Glu—Ala—Ala—Phe—Gln—

Lys—Leu—Met—Ser—Asn—Leu—Asp—Ser—Asn—Arg—Asp—Asn—Glu—Val—

Asp—Phe—Gln—Glu—Tyr—Cys—Val—Phe—Leu—Ser—Cys—Ile—Ala—Met—

Met—Cys—Asn—Glu—Phe—Phe—Glu—Gly—Phe—Pro—Asp—Lys—Gln—Pro—

Arg—Lys—Lys.

Other mammalian mts-1 genes are also contemplated.

The present invention also relates to a useful animal model system of metastasis for screening potential antimetastatic drugs and for developing therapeutic regimens for cancer treatment. This model system includes non-metastasizing and metastasizing tumors that are maintained by sequential transplantation from one mouse or rat to another, as well as cultured cell lines, derived from these tumors, which retain the metastatic or non-metastatic potential of their parental tumors. Hence, these tumors or cell lines may be transplanted or injected into mice or rats to generate benign or metastatic tumors. Concurrently, drugs or other therapies with anti-tumorigenic or anti-metastatic metastatic potential, may be introduced into the animal to test whether the formation of the metastatic and benign tumors is suppressed. This model system has high utility because of the predictable metastatic potential of the tumors and cell lines therein and also because cell lines of differing metastatic potential were derived from the same parental tumor and hence have a common genetic and phenotypic make-up, except for their metastatic potential. Hence the animal model system of the current invention is highly controlled and has predictable metastatic potential.

The human mts-1 gene of the present invention was obtained by use of mouse and rat mts-1 clones previously obtained by the present inventors. The mouse and rat mts-1 genes were obtained from cDNA libraries made from metastatic mouse and rat tumor RNAs. The mouse mts-1 gene has been obtained from a highly metastatic cell line derived from a spontaneous mouse mammary carcinoma (CSML-100), while the mts-1 rat gene utilized in the present invention was from a highly metastatic thyroid carcinoma, IR-6. Both the mouse and rat mts-1 genes were obtained by differential hybridization of the respective cDNA libraries with a probe made from a pool of mRNAs from highly metastatic tissues, and a probe made from a pool of mRNAs from low metastatic tissues.

The human mts-1 gene was obtained from a cDNA library made by the present inventors from mRNA purified from cultured HeLa cells and from cultured melanoma Wm64 cells. Clones hybridizing strongly to a mouse mts-1 cDNA probe can be identified as being the human mts-1 homologue by DNA sequencing. Alternatively, a cDNA can be obtained by reverse transcription and polymerase chain reaction using mRNA purified from metastatic cells, e.g. as provided in Miller 1988 Ann. Rev. Microbiol. 42:177.

There is a difference of seven amino acids between the mouse and human mts-1 proteins, demonstrating that while the mouse and human proteins are functionally related they are not identical structurally.

In another embodiment, the mouse, rat, and, in particular, the human mts-1 genes of the present invention have been subcloned into convenient replicable vectors for production of large amounts of mts-1 DNA and large amounts of sense or antisense mts-1 RNA. Convenient replicable vectors comprise the gene or a DNA fragment thereof of the present invention, an origin of replication which is operable in the contemplated host, and, preferably, a selectable marker, for example, an antibiotic resistance marker. Many of these vectors are based on pBR322. Convenient replicable vectors which allow synthesis of RNA from the DNA of interest include Bluescript™ (commercially available from Stratagene), pTrcHisB (Invitrogen) and others that are well known in the art.

The present invention also contemplates replicable expression vectors allowing a higher level of expression of the mammalian mts-1 protein. Replicable expression vectors as described herein are generally DNA molecules engineered for controlled expression of a desired gene, especially high level expression where it is desirable to produce large quantities of a particular gene product, or polypeptide. The vectors encode promoters and other sequences to control expression of that gene, the gene being expressed, and an origin of replication which is operable in the contemplated host. Preferably the vector also encodes a selectable marker, for example, antibiotic resistance. Replicable expression vectors can be plasmids, bacteriophages, cosmids and viruses. Any expression vector comprising RNA is also contemplated.

Preferred vectors of the present invention are derived from eukaryotic sources. Expression vectors that function in tissue culture cells are especially useful, but yeast vectors are also contemplated. These vectors include yeast plasmids and minichromosomes, retrovirus vectors, BPV (bovine papilloma virus) vectors, baculovirus vectors, SV40 based vectors and other viral vectors. SV40-based vectors and retrovirus vectors (e.g., murine leukemia viral vectors) are preferred. Tissue culture cells that are used with eukaryotic replicable expression vectors include Sf21 cells, CV-1 cells, COS-1 cells, NIH3T3 cells, mouse L cells, HeLa cells and such other cultured cell lines known to one skilled in the art.

A baculovirus expression system can be used to produce large amounts of mts-1 polypeptides in cultured insect cells. The post-translational processing of polypeptides produced in such insect cells is similar to that of mammalian cells. Production of polypeptides in insects is therefore advantageous, particularly when one seeks to mimic the exact function or antigenic properties of the natural polypeptide. Moreover, mts-1 polypeptides expressed in the baculovirus system are produced without the need for a fused heterologous polypeptide because the mts-1 start codon is used as the translational start site.

Methods for producing polypeptides in the baculovirus expression system are known to the skilled artisan. See for example Miller 1988 Ann. Rev. Microbiol. 42:177. In general, a modified *Autographa californica* nuclear polyhedrosis virus propagated in Sf21 cells is used for polypeptide expression. This modified virus is produced by cotransfection of a small transfer vector, encoding an mts-1 polypeptide, with a viral expression vector which has been linearized within an essential gene. Once inside the cell, the linearized expression vector can undergo recombination with the transfer vector or simply recircularize. However, only recombination gives rise to viable viruses because the function of the essential gene is lost by recircularization. Recombinant expression viruses are detected by formation of plaques. The present invention also contemplates prokaryotic vectors that may be suitable for expression of the mammalian mts-1 gene, including bacterial and bacteriophage vectors that can transform such hosts as *E. coli, B. subtilis*, Streptomyces sps. and other microorganisms. Many of these vectors are based on pBR322 including Bluescript™ (commercially available from Stratagene) and are well known in the art. Bacteriophage vectors that are used in the invention include lambda and M13.

Sequence elements capable of effecting expression of the human mts-1 gene include promoters, enhancer elements, transcription termination signals and polyadenylation sites. Promoters are DNA sequence elements for controlling gene expression, in particular, they specify transcription initiation sites. Prokaryotic promoters that are useful include the lac promoter, the trp promoter, and $P_L$ and $P_R$ promoters of lambda and the T7 polymerase promoter. Eukaryotic promoters are especially useful in the invention and include promoters of viral origin, such as the SV40 late promoter and the Moloney Leukemia Virus LTR, Murine Sarcoma Virus (MSV) LTR, yeast promoters and any promoters or variations of promoters designed to control gene expression, including genetically-engineered promoters. Control of gene expression includes the ability to regulate a gene both positively and negatively (i.e., turning gene expression on or off) to obtain the desired level of expression.

The replicable expression vectors of the present invention can be made by ligating part or all of the mts-1 coding region in the sense or antisense orientation to the promoter and other sequence elements being used to control gene expression. This juxtapositioning of promoter and other sequence elements with the mts-1 gene allows the production of large amounts of sense or antisense mts-1 mRNA. Large amounts of the mts-1 protein can also be produced which are useful not only for anti-mts-1 antibody production but also for analysis of the function of mts-1 in metastatic cancer as well as for designing therapies for metastatic cancer.

As one example of an appropriate expression vector for the human mts-1 gene, the present invention provides the pEMSVscribe2 vector which expresses the human mts-1 gene of this invention.

Figure 10A:
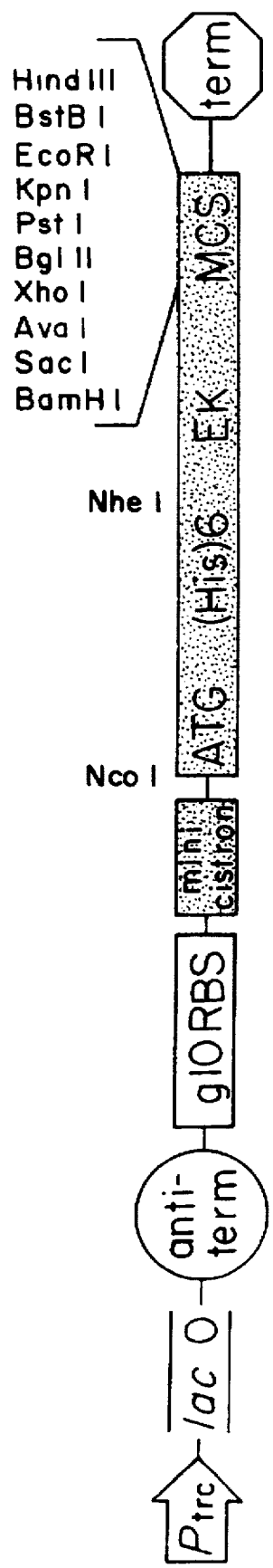
FIG. 10a depicts a diagram of the more important regions of the pTrcHis B expression vector utilized to produce a histidine-mts-1 fusion protein. The murine mts-1 cDNA was subcloned into pTrcHis B at the BamHI-KpnI site to generate pTBM1.

In another example, large quantities of the mts-1 specific protein were expressed in an *E. coli* host using the inducible bacterial vector pTrcHisB (FIG. 10a). Murine mts-1 cDNA was subcloned in frame into a BamHI-KpnI site with the multiple cloning site of pTrcHisB to generate plasmid pTBM1. The fusion protein expressed by pTBM1 has 6 tandem histidine residues which allow easy purification of the fusion protein because of the high affinity of such tandem histidines for a $Ni^{++}$ charged resin. The fusion protein also has an enterokinase specific cleavage site permitting removal of the histidines from the mts-1 protein product. Expression of the mts-1 fusion protein encoded by pTBM1 can be induced by IPTG. Similar human mts-1 cDNA constructs have also been generated.

Therefore, one skilled in the art has available many choices of replicable expression vectors, compatible hosts and well-known methods for making and using the vectors. Recombinant DNA methods are found in any of the myriad of standard laboratory manuals on genetic engineering.

The present invention is also directed to the detection of metastatic cancer in tissue specimens by use of the mts-1 DNA as a nucleic acid probe for detection of mts-1 mRNA, or by use of antibodies directed against the mts-1 protein.

The nucleic acid probe of the present invention may be any portion or region of a mammalian mts-1 RNA or DNA sufficient to give a detectable signal when hybridized to mts-1 mRNA derived from a tissue sample. The nucleic acid probe produces a detectable signal because it is labeled in some way, for example because the probe was made by incorporation of nucleotides linked to a "reporter molecule".

A "reporter molecule", as used in the present specification and claims, is a molecule which, by its chemical nature, provides an analytically identifiable signal allowing detection of the hybridized probe. Detection may be either quantitative or quantitative. The most commonly used reporter molecules in this type of assay are either enzymes, fluorophores or radionuclides covalently linked to nucleotides which are incorporated into a mts-1 DNA or RNA. Commonly used enzymes include horseradish peroxidase, alkaline phosphatase, glucose oxidase and β-galactosidase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for horseradish peroxidase, 1,2-phenylenediamine, 5-aminosalicyclic acid or tolidine are commonly used.

Incorporation into a mts-1 DNA probe may be by nick translation, random oligo priming, by 3' or 5' end labeling, by labeled single-stranded DNA probes using single-stranded bacteriophage vectors (e.g. M13 and related phage), or by other means, (Sambrook et al., 1989, Molecular Cloning, A Laboratory Manual. Cold Spring Harbor Laboratory Press. Pages 10.1–10.70). Incorporation of a reporter molecule into a mts-1 RNA probe may be by synthesis of mts-1 RNA using T3, T7, Sp6 or other RNA polymerases (Sambrook et al., supra: 10.27–10.37).

Detection or diagnosis of metastatic cancer by the nucleic acid probe of the present invention can be by a variety of hybridization techniques which are well known in the art. In one embodiment, patient tissue specimens are sectioned and placed onto a standard microscope slide, then fixed with an appropriate fixative. The mts-1 RNA or DNA probe, labeled by one of the techniques described above, is added. The slide is then incubated at a suitable hybridization temperature (generally 37° C. to 55° C.) for 1–20 hours. Non-hybridized RNA or DNA probe is then removed by extensive, gentle washing. If a non-radioactive reporter molecule is employed in the probe, the suitable substrate is applied and the slide incubated at an appropriate temperature for a time appropriate to allow a detectable color signal to appear as the slide is visualized under light microscopy. Alternatively, if the mts-1 probe is labeled radioactively, slides may be dipped in photoemulsion after hybridization and washing, and the signal detected under light microscopy after several days, as exposed silver grains.

Metastatic cancer can also be detected from RNA derived from tissue specimens by the mts-1 nucleic acid probe. RNA from specimens can be fixed onto nitrocellulose or nylon filters, and well-known filter hybridization techniques may be employed for detection of mts-1 gene expression. Specimen mRNA can be purified, or specimen cells may be simply lyzed and cellular mRNA fixed unto a filter. Specimen mRNA can be size fractionated through a gel before fixation onto a filter, or simply dot blotted unto a filter.

In another embodiment, the mts-1 nucleic acid detection system of the present invention also relates to a kit for the detection of mts-1 mRNA. In general, a kit for detection of mts-1 mRNA contains at least one mts-1 nucleic acid. Such an mts-1 nucleic acid can be a probe having an attached reporter molecule or the mts-1 nucleic acid can be unlabelled. The unlabelled mts-1 nucleic acid can be modified by the kit user to include a reporter molecule or can act as a substrate for producing a labelled mts-1 probe, for example by nick translation or RNA transcription.

In another embodiment, the kit is compartmentalized: a first container can contain mts-1 RNA at a known concentration to act as a standard or positive control, a second container can contain mts-1 DNA suitable for synthesis of a detectable nucleic acid probe, and a third and a fourth container can contain reagents and enzymes suitable for preparing said mts-1 detectable probe. If the detectable nucleic acid probe is made by incorporation of an enzyme reporter molecule, a fifth or sixth container can contain a substrate, or substrates, for the enzyme provided.

In accordance with the present invention, the mts-1 protein or portions thereof can be used to generate antibodies useful for the detection of the mts-1 protein in clinical specimens. Such antibodies may be monoclonal or polyclonal. Additionally, it is within the scope of this invention to include second antibodies (monoclonal or polyclonal) directed to the anti-mts-1 antibodies. The present invention further contemplates use of these antibodies in a detection assay (immunoassay) for the mts-1 gene product.

The present invention further contemplates antibodies directed against the mammalian, including rat, mouse and human, mts-1 proteins or polypeptides. These antibodies may be generated by using the entire mts-1 protein as an antigen or by using short peptides, encoding portions of the mts-1 protein, as antigens. When peptides are contemplated they have at least about 4 amino acids and preferably at least about 10 amino acids.

Preferably, specific peptides encoding unique portions of the mammalian mts-1 gene are synthesized for use as antigens for obtaining mts-1 antibodies. This is done because mts-1 encodes a calcium binding domain whose sequence, and hence antigenicity, is similar to other calcium binding proteins. By utilizing peptides encoding sequences lying outside the calcium binding domain, cross-reactivity of the anti-mts-1 antibodies towards other calcium binding proteins easily can be avoided. Accordingly, peptide sequences are tested for sequence homologies by searching protein sequence data banks before peptides are actually synthesized. Among the various mts-1 peptides that can be used, four peptides encoding a portion of the human mts-1 sequence shown below, have already been used to generate antibodies:

1) Unique peptide encoding amino acids 2–11 of the mts-1 protein (SEQ ID NO:4): Ala-Cys-Pro-Leu-Glu-Lys-Ala-Leu-Asp-Val;
2) Peptide encoding the calcium binding domain of the mts-1 protein (amino acids 22–37, SEQ ID NO:5): Lys-Glu-Gly-Asp-Lys-Phe-Lys-Leu-Asn-Lys-Ser-Glu-Leu-Lys-Glu-Leu;
3) Unique peptide encoding amino acids 42–54 of the mts-1 protein (SEQ ID NO:6): Leu-Pro-Ser-Phe-Leu-Gly-Lys-Arg-Thr-Asp-Glu-Ala-Ala;
4) Unique peptide encoding amino acids 87–101 of mts-1 protein (SEQ ID NO:7): Asn-Glu-Phe-Phe-Glu-Gly-Phe-Pro-Asp-Lys-Gln-Pro-Arg-Lys-Lys.

Polyclonal antibodies directed against the mts-1 protein are prepared by injection of a suitable laboratory animal with an effective amount of the peptide or antigenic component, collecting serum from the animal, and isolating specific sera by any of the known immunoadsorbent techniques. Animals which can readily be used for producing polyclonal anti-mts-1 antibodies include chickens, mice, rabbits, rats, goats, horses and the like. Chickens are preferred because a better immune response can be obtained and because antibodies can be collected from eggs rather than by bleeding. Although the polyclonal antibodies produced by this method are utilizable in virtually any type of immunoassay, they are generally less favored because of the potential heterogeneity of the product.

The use of monoclonal antibodies in the diagnostic or detection assays of the present invention is particularly preferred because large quantities of antibodies, all of similar reactivity, may be produced. The preparation of hybridoma cell lines for monoclonal antibody production is done by fusing an immortal cell line and the antibody producing lymphocytes. This can be done by techniques which are well known to those who are skilled in the art. (See, for example, Harlow, E. and Lane, D., *Antibodies: A Laboratory Manual*, Cold Spring Harbor Press, 1988; or Douillard, J. Y. and Hoffman, T., "Basic Facts About Hybridomas", in *Compendium of Immunology Vol. II*, L. Schwartz (Ed.), 1981.

Unlike the preparation of polyclonal sera, the choice of animal for monoclonal antibody preparation is dependent on the availability of appropriate immortal cell lines capable of fusing with the monoclonal antibody producing lymphocytes derived from the immunized animal. Mouse and rat have been the animals of choice for hybridoma technology and are preferably used. Humans can also be utilized as sources for antibody producing lymphocytes if appropriate immortalized human (or nonhuman) cell lines are available. For the purpose of making the monoclonal antibodies of the present invention, the animal of choice may be injected with from about 0.01 mg to about 20 mg of the purified mts-1 antigen. Usually the injecting material is emulsified in Freund's complete adjuvant. Boosting injections are generally also required. The separate immortalized cell lines obtained by cell fusion may be tested for antibody production by testing the cell culture media for the ability to find the appropriate antigen.

Lymphocytes can be obtained by removing the spleen or lymph nodes of immunized animals in a sterile fashion. Alternately, lymphocytes can be stimulated or immunized in vitro, as described, for example, in C. Reading *J. Immunol. Meth.* 53:261–291 1982. To immortalize the monoclonal antibody producing lymphocytes, the lymphocytes must be fused to immortalized cells. A number of cell lines suitable for fusion have been developed, and the choice of any particular line for hybridization protocols is directed by any one of a number of criteria such as speed, uniformity of growth characteristics, deficiency of its metabolism for a component of the growth medium, and potential for good fusion frequency. Intraspecies hybrids, particularly between like strains, work better than interspecies fusions.

Several cell lines are available, including mutants selected for the loss of ability to create myeloma immunoglobulin. Included among these are the following mouse myeloma lines: MPC$_{11}$-X45-6TG, P3 NS1/1-Ag4-1, P3-X63-Ag14 (all BALB/C derived), Y3'Agl.2.3 (rat), and U266 (human).

Cell fusion can be induced either by virus, such as Epstein-Barr or Sendai virus, or polyethylene glycol. Polyethylene glycol (PEG) is the most efficacious agent for the fusion of mammalian somatic cells. PEG itself may be toxic for cells, and various concentrations should be tested for effects on viability before attempting fusion. The molecular weight range of PEG may be varied from 1,000 to 6,000. It give best results when diluted to from about 20% to about 70% w/w in saline or serum-free medium. Exposure to PEG at 37° C. for about 30 seconds is preferred in the present case, utilizing murine cells. Extremes of temperature (i.e. about 45° C.) are avoided, and preincubation of each component of the fusion system at 37° C. prior to fusion gives optimum results. The ratio between lymphocytes and immortalized cells optimized to avoid cell fusion amongst lymphocytes ranges of from about 1:1 to about 1:10.

The successfully fused cells can be separated from the immortalized cell line by any technique known by the art. The most common and preferred method is to choose an immortalized cell line which is Hypoxanthine Guanine Phosphoribosyl Transferase (HGPRT) deficient. Since these cells will not grow in an aminopterin-containing medium, only hybrids of lymphocytes and immortalized cells will grow. The aminopterin-containing medium is generally composed of hypoxanthine $1\times10^{-4}$M, aminopterin $1\times10^{5}$M, and thymidine $3\times10^{-5}$M, commonly known as the HAT medium. Fused cells are generally grown for two weeks and then fed with either regular culture medium or hypoxanthine, thymidine-containing medium.

The fused cell colonies are then tested for the presence of antibodies that recognize the mts-1 protein. Detection of hybridoma antibodies can be performed using an assay where the antigen is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrid cells can be carried out after 20–25 days of cell growth in selected medium. Cloning can be performed by cell limiting dilution in fluid phase or by directly selecting single cells growing in semi-solid agarose. For limiting dilution, cell suspensions are diluted serially to yield a statistical probability of having only one cell per well. For the agarose techniques, hybrids are seeded in a semisolid upper layer, over a lower layer containing feeder cells. The colonies from the upper layer may be picked up and eventually transferred to wells.

Antibody-secreting hybrid cells can be grown in various tissue culture flasks, yielding supernatants with variable concentrations of antibodies. In order to obtain higher concentrations, hybrid cells may be transferred into animals to obtain inflammatory ascites. Antibody-containing ascites can be harvested 8–12 days after intraperitoneal injection. The ascites contain a higher concentration of antibodies but include both monoclonals and immunoglobulins from the inflammatory ascites. Antibody purification may then be achieved by, for example, affinity chromatography.

One embodiment of the present invention is directed to a method for diagnosing metastatic cancer by contacting or applying an antibody reactive with an mts-1 polypeptide to a tissue or blood sample taken from an individual to be tested for metastatic cancer. Formation of an antigen-antibody complex in this immunoassay is diagnostic of metastatic cancer.

In a preferred embodiment, the present invention provides a method for diagnosing metastatic cancer which involves contacting serum from an individual to be tested for such cancer with an antibody reactive with a mammalian mts-1 protein or an antigenic fragment thereof, for a time and under conditions sufficient to form an antigen-antibody complex, and detecting the antigen-antibody complex.

The presence of the mts-1 protein, or its antigenic components, in a patient's serum, tissue or biopsy sample can be detected utilizing antibodies prepared as above, either monoclonal or polyclonal, in virtually any type of immunoassay. A wide range of immunoassay techniques are available as can be seen by reference to Harlow, et al. (*Antibodies: A Laboratory Manual*, Cold Spring Harbor Press, 1988) and U.S. Pat. Nos. 4,016,043 and 4,424,279. This, of course, includes both single-site and two-site, or "sandwich" of the non-competitive types, as well as in traditional competitive binding assays. Sandwich assays are among the most useful and commonly used assays. A number of variations of the sandwich assay technique exist, and all are intended to be encompassed by the present invention. Briefly, in a typical forward assay, an unlabeled antibody is immobilized in a solid substrate and the sample to be tested brought into contact with the bound molecule. After a suitable period of incubation, for a period of time sufficient to allow formation of an antibody-antigen binary complex, a second antibody, labeled with a reporter molecule capable of producing a detectable signal is then added and incubated, allowing tie sufficient for the formation of a ternary complex of antibody-labeled antibody. Any reacted material is washing way, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labeled antibody are added simultaneously to the bound antibody, or a reverse assay in which the labeled antibody and sample to be tested are first combined, incubated and then added to the unlabeled surface bound antibody. These techniques are well known to those skilled in the art, and then possibly of minor variations will be readily apparent. As used herein, "sandwich assay" is intended to encompass all variations on the basic two-site technique.

The mts-1 protein may also be detected by a competitive binding assay in which a limiting amount of antibody specific for the mts-1 protein is combined with specified volumes of samples containing an unknown amounts of the mts-1 protein and a solution containing a detectably labeled known amount of the mts-1 protein. Labeled and unlabeled molecules then compete for the available binding sites on the antibody. Phase separation of the free and antibody-bound molecules allows measurement of the amount of label present in each phase, thus indicating the amount of antigen or hapten in the sample being tested. A number of variations in this general competitive binding assays currently exist.

In any of the known immunoassays, for practical purposes, one of the antibodies or the antigen will be typically bound to a solid phase and a second molecule, either the second antibody in a sandwich assay, or, in a competitive assay, the known amount of antigen, will bear a detectable label or reporter molecule in order to allow visual detection of an antibody-antigen reaction. When two antibodies are employed, as in the sandwich assay, it is only necessary that one of the antibodies be specific for the mts-1 protein or its antigenic components. The following description will relate to a discussion of a typical forward sandwich assay; however, the general techniques are to be understood as being applicable to any of the contemplated immunoassays.

In the typical forward sandwich assay, a first antibody having specificity for the mts-1 protein or its antigenic components is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art and generally consist of cross-linking covalently binding or physically adsorbing the molecule to the insoluble carrier. Following binding, the polymer-antibody complex is washed in preparation for the test sample. An aliquot of the sample to be tested is then added to the solid phase complex and incubated at a suitable temperature ranging from about 4° C. to about 37° C. (for example 25° C.) for a period of time sufficient to allow binding of any subunit present in the antibody. The incubation period will vary but will generally be in the range of about 2–40 minutes to several hours. Following the incubation period, the antibody subunit solid phase is washed and dried and incubated with a second antibody specific for a portion of a mts-1 hapten. The second antibody is linked to a reporter molecule which is used to indicate the binding of the second antibody to the hapten.

By "reporter molecule", as used in the present specification and claims, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, β-galactosidase and alkaline phosphates, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine, 5-aminosalicyclic acid, or tolidine are commonly used. It is also possible to employ fluorogenic substrates, which yield a fluorescent product rather than the chromogenic substrates noted above. In all cases, the enzyme-labeled antibody is added to the first antibody hapten complex, allowed to bind, and then the excess reagent is washed away. A solution containing the appropriate substrate is then added to the ternary complex of antibody-antigen-antibody. The substrate will react with the enzyme linked to the second antibody, giving a qualitative visual signal, which may be further quantitated, usually spectrophotometrically, to give an indication of the amount of hapten which was present in the sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic color visually detectable with a light microscope. The fluorescent labeled antibody is allowed to bind to the first antibody-hapten complex. After washing off the unbound reagent, the remaining ternary complex is then exposed to the light of the appropriate wavelength, the fluorescence observed indicates the presence of the hapten of interest. Immunofluorescence techniques are very well established in the art. However, other reporter molecules, such as radioisotope, chemiluminescent or bioluminescent molecules, may also be employed. It will be readily apparent to the skilled technician how to vary the procedure to suit the required purpose.

In another embodiment, the antibodies directed against the mts-1 protein may be incorporated into a kit for the detection of the mts-1 protein. Such a kit may encompass any of the detection systems contemplated and described herein, and may employ either polyclonal or monoclonal antibodies directed against the mts-1 protein. Both mts-1 antibodies complexed to a solid surface described above or soluble mts-1 antibodies are contemplated for use in a detection kit. A kit of the present invention has at least one container having an antibody reactive with a mammalian mts-1 polypeptide. However, the present kits can have other components. For example, the kit can be compartmentalized: the first container contains mts-1 protein as a solution, or bound to a solid surface, to act as a standard or positive control, the second container contains anti-mts-1 primary antibodies either free in solution or bound to a solid surface, a third container contains a solution of secondary antibodies covalently bound to a reporter molecule which are reactive against either the primary antibodies or against a portion of the mts-1 protein not reactive with the primary antibody. A fourth and fifth container contains a substrate, or reagent, appropriate for visualization of the reporter molecule.

The subject invention therefore encompasses polyclonal and monoclonal antibodies useful for the detection of mts-1 protein as a means of diagnosing metastatic cancer. Said antibodies may be prepared as described above, then purified, and the detection systems contemplated and described herein employed to implement the subject invention.

The present invention also contemplates treating metastatic cancers and tumors by inactivating, destroying or nullifying the mts-1 gene or protein, or cells expressing the mts-1 gene. The treatment of cancer, as described in the specification and claims, contemplates preferably lung, liver, kidney, thyroid, mammary gland, leukemic, pancreatic, endometrial, ovarian, cervical, skin, colon or lymphoid cancers. For example, the antibodies, prepared as described above, may be utilized to inactivate mts-1 protein expressing cells: either unconjugated anti-mts-1 antibodies or anti-mts-1 antibodies conjugated to a toxin may be employed in the therapy of cancer.

Moreover, the present invention provides a method of inhibiting metastasis in a cancerous cell by providing to the cancerous cell a nucleic acid encoding an antisense mts-1 nucleotide sequence. For example, such an antisense nucleic acid can have at least 10 nucleotides of the antisense strand of SEQ ID NO:1 or SEQ ID NO:3. Preferably, the antisense mts-1 nucleic acids of the present invention have at least 15 or 17 nucleotides.

In one embodiment, this method employs an expression vector including a nucleic acid encoding an antisense nucleotide sequence for mts-1 operably linked to a segment of the vector which can effect expression of an antisense mts-1 RNA. Any of the foregoing expression vectors which can express high levels of mts-1 RNA can be used for this method including, e.g., pTrcHis.

According to the present invention, antisense mts-1 nucleic acids can inhibit metastatic cancer by binding to sense mts-1 mRNA. Such binding can either prevent translation of mts-1 protein or destroy mts-1 sense mRNA, e.g., through the action of RNaseH. Accordingly, less mts-1 protein is available to potential metastatic tumor cells and metastasis of these cells is prevented.

Another embodiment of the present invention contemplates pharmaceutical compositions containing, for example, an antibody reactive with a mammalian mts-1 polypeptide, an antisense mts-1 nucleic acid or the mts-1 protein. The mts-1 protein is known to bind calcium and has a role in the growth of cells (Linzer, et al., Proc. Natl. Acad. Sci. U.S.A. 80:4271–4275, 1983; Jackson-Grusby, et al., Nuc. Acids. Res. 15:6677–6689; Goto et al., J. Biochem. 103:48–53, 1988). The mts-1 protein is also very closely related to 42A, a gene thought to have a role in nerve cell growth (Masiakowski, et al. Proc. Natl. Acad. Sci. U.S.A. 85:1277–1281, 1988). The mts-1 protein may also have a role in the differentiation of myoepithelial cells (Barraclough, et al., J. Mol. Biol. 198:13–20, 1987). Hence the human mts-1 protein may be clinically useful, for example, in stimulating cells in general or preferably, nerve cells, to grow, and further, in promoting the differentiation of myoepithelial cells.

The active ingredients of a pharmaceutical composition containing the mts-1 protein or anti-mts-1 antibodies and antisense mts-1 nucleic acids (i.e. anti-cancer reagents) are contemplated to exhibit effective therapeutic activity, for example, in promoting cell growth, or for treating cancer, respectively. Thus the active ingredients of the therapeutic compositions containing mts-1 protein cell proliferative activity or anti-cancer reagents, are administered in therapeutic amounts which depend on the particular disease. For example, from about 0.5 μg to about 2000 mg per kilogram of body weight per day may be administered. The dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in a convenient manner such as by the oral, intravenous (where water soluble), intramuscular, subcutaneous, intranasal, intradermal or suppository routes. Depending on the route of administration, the active ingredients which comprise mts-1 proteins or anti-cancer reagents may be required to be coated in a material to protect said ingredients from the action of enzymes, acids and other natural conditions which may inactivate said ingredients.

For example, the low lipophilicity of mts-1 protein, and some anti-cancer reagents, may allow them to be destroyed in the gastrointestinal tract by enzymes capable of cleaving peptide or nucleotide bonds and in the stomach by acid hydrolysis. In order to administer mts-1 protein or anti-cancer reagents by other than parenteral administration, they should be coated by, or administered with, a material to prevent its inactivation. For example, mts-1 protein or anti-cancer reagents may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DFP) and trasylol. Liposomes include water-in-oil-in-water P40 emulsions as well as conventional liposomes.

The active compounds may also be administered parenterally or intraperitoneally. Dispersions can also be prepared in glycerol, liquid polyethylene glycols, and mixtures thereof, and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extend that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, sorbic acid, thimerosal, and the like. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient plus any additional desired ingredient from previously sterile-filtered solution thereof.

When the mts-1 protein or anti-cancer reagents are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains between about 0.5 µg and 2000 µg of active compound.

The tablets, troches, pills, capsules, and the like, as described above, may also contain the following: a binder such as gum gragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, lactose or saccharin may be added or a flavoring agent such as peppermint, oil or wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of the active material calculated to produce the desired therapeutic effect in association with the required pharmaceutical carrier. The specification for the novel dosage unit forms of the invention are dictated by and directly depending on (a) the unique characteristics of the active material and the particular therapeutic effect to be achieved, and (b) the limitations inherent in the art of compounding such as active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 µg to about 2000 µg. Expressed in proportions, the active compound is generally present in from about 10 µg to about 2000 mg/ml of carrier. In the case of compositions containing supplementary active ingredients, the dosages are determined by reference to the usual dose and manner of administration of the said ingredients.

As used herein "pharmaceutically acceptable carrier" includes any and all solvents, dispersion media, coatings, antibacterial and antifungal agents, isotonic and adsorption delaying agents, and the like. The use of such media gents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

Another embodiment of the present invention relates to the animal tumors and tumor cell lines developed in accordance with the present invention which are useful as model systems of the metastatic process. These tumors and cell lines can be utilized for screening anti-metastatic drugs and for developing therapeutic regimens for the treatment of malignant cancer is provided by the present invention. The tumors provided by the present invention include the IR6 and IR4 tumors. The tumor cell lines provided by the present invention include CSML-0, CSML-50, CSML-100, HMC-0, HMC-Lr, T9, T36, LMEC, PCC4c-P, PCC4c-B, PCC4c-107, IR6CL$_1$, IR4 CL, ELCL$_1$, TRCL$_1$ and the murine lung carcinoma Line 1.

The tumors or cell lines of the present invention each have a highly predictable metastatic potential; however the metastatic potentials of related, but separate, tumors or cell lines can be very different. The properties, and metastatic potentials, of the tumors and cell lines of the present invention are fully described in Examples 1, 2, 3 and 12 and in Tables 1 and 2. While these tumors and cell lines were derived from mouse mammary carcinomas as well as rat thyroid and epithelial carcinomas, they are useful for the development of a variety of human cancer therapies, for several reasons. First, cancer cells all have similar properties, including, for example, unrestrained growth and lack of contact inhibition, which suggests that the process of cancer development is similar in all cancers. Second, the morphologies and biochemical properties of the tumors developed after injection of these tumor-derived cells are identical to analogous tumors in humans. Hence, potential anti-cancer therapies or drugs may effectively be screened by employing the animal model system of the current invention.

The utility of these unique tumors and cell lines is apparent to one skilled in the art. Briefly, animals are injected with tumors or tumor-derived cells which have a predictable metastatic potential. A proportion of the animals are treated with a potential anti-cancer drug or therapy. After a suitablt period of time, all animals are sacrificed and the tissues of both treated and non-treated animals are examined for the development of primary and secondary (metastatic) tumors. If a therapeutic regimen is successful, the treated animals should have a much lower incidence of tumor formation.

Both mouse and rat model systems are provided by the present invention for the development of cancer therapy. A spontaneous mouse mammary carcinoma has been used to generate different cell lines with low, intermediate and high incidences of metastasis. This is done by intramuscular transplantation or subcutaneous tail transplantations of the original spontaneous mammary tumor cells into syngeneic mice. Intramuscular transplantation has yielded a cell line called CSML-0 which has low metastatic potential. Solitary lung metastasis are detected in less than 10% of CSML-0 injected animals sacrificed because of a moribund condition. The highly metastatic CSML-100 cell line has been generated by selection of the metastatic phenotype through successive subcutaneous transplantations of CSML metastatic cells into the tail. The CSML-50 cell line, selected during the generation of CSML-100, has an intermediate level of metastatic potential.

A variety of rat tumors have been generated by irradiating normal Fischer 344 rat thyroid cell suspensions and then transplanting these cells into rats. Grafts of non-irradiated thyroid cells develop into morphologically and functionally normal thyroid tissue after transplantation into Fischer 344 syngenic rats, if elevated levels of thyroid stimulating hormone are also provided. Irradiation of thyroid cell suspensions before transplantation has produced a series of rat thyroid carcinomas which are histopathologically identical to human counterparts. For example, the IR6 tumor, generated in accordance with the present invention, is highly metastatic, while the IR4 tumor has low metastatic potential. Both tumors are structurally and histologically identical to corresponding human tumors (FIG. 7).

The extensive variety of tumors and cell lines, and the varying metastatic potential of these tumors and cell lines, provides mouse and rat model systems amenable to carefully controlled studies directed towards the dissection of the metastatic process. Therapeutic regimens for treatment of malignant cancer can be developed by controlled studies of groups of animals injected with cells of high, low and intermediate metastatic potential. A drug, or pharmaceutical composition suspected of having anti-metastatic potential, may be used to treat a proportion of animals from each group. The incidence of metastasis amongst the animals receiving the drug or pharmaceutical composition may be compared with the incidence amongst animals not receiving treatment. Therefore, the present invention provides an animal system for distinguishing effective anti-metastatic drugs and therapies from those that are ineffective.

The Examples serve to further illustrate the invention without in any way limiting same.

EXAMPLE 1

Materials And Methods

1. Medium

Dulbecco's modified Eagle's medium (DMEM) containing 10% fetal calf serum (FCS) was used for all cell lines. Cells were passed weekly.

2. Metastatic activity

Metastatic activity was determined by intramuscular injection of $1\times10^4$ to $1\times10^6$ tumor cells per tumor cell line in 10–15 mice. Either A/Sn or A/J mice were used.

For A/Sn mice, cultured tumor cells were trypsinized, rinsed and suspended in sterile Hanks' salt solution. A total of $1\times10^6$ cells in 0.3 ml of Hanks' solution was injected subcutaneously into each 8 to 10 week old A/Sn mouse. The mice were killed 4–5 weeks after tumor inoculation and the number of lung metastasis was counted. Non-metastatic cell lines were defined as cell lines that did not result in visible metastases. Highly metastatic lines under the same conditions gave rise to multiple metastases in target organs of each mouse.

Female A/J mice (4–6 weeks old) were injected either with $1\times10^4$ cells intravenously through the tail vein or with $1\times10^6$ cells subcutaneously into the abdomen. Fifteen days following intravenous injection and 4–6 weeks after subcutaneous injection, the animals were sacrificed and the lung metastases were counted.

3. Mouse Tumor Cell Lines

CSML-0, CSML-50 and CSML-100 tumor cell lines were established in accordance with the present invention from spontaneous mammary adenocarcinomas of A/Sn mice. These cell lines are described in more detail in Example 2.

HMC-0 and HMV-Lr are tumor cell lines which were also established from spontaneous mammary adenocarcinomas of A/Sn mice. T-9, as well as T-36 and its variant LMEC, are coupled sublines of two original tumors which were induced by ectopic transplantation of 6–7 day-old gestation syngeneic embryos to CBA/J and A/Sn mice.

Cell lines, PCC4c-P, PCC4,-B and PCC4c-107 were derived from PCC4-Blangy, PCC4-Pasteur and PCC4-107 teratocarcinomas, respectively.

A murine lung carcinoma, Line 1, cell line is highly metastatic, however when Line 1 cells are grown in the presence of the 3% DMSO, these cells lose their metastatic potential.

Some of the properties of the above cell lines, and their metastatic potential, are described in Table 1.

TABLE 1

Metastatic Potential of Analyzed Mouse Tumors and Mouse Tumor Cell Lines

| Tumors and Cell Lines[a] | Spontaneous Metastases | Target Organs |
|---|---|---|
| Mammary carcinosarcoma | | |
| CSML-0 | low metastatic[b] | lung |
| CSML-50 | 50% | lung |
| CSML-100 | high metastatic[c] | lung |
| Mammary Solid Carcinoma | | |
| HMC-0 | low metastatic | liver[d] |
| HMC-Lr | high metastatic | liver[d] |
| Teratocarcinoma cell line | | |
| PCC4$_e$-B | nonmetastatic | — |
| PCC4$_e$-P | nonmetastatic | — |
| PCC4$_e$-107 | nonmetastatic | — |
| C12- | nonmetastatic | — |
| Embryocarcinoma, T-36 node | 50% | lymph |
| Cell line derived from T-36, T-36$_c$ node | 50% | lymph |
| Embryocarcinoma, LMEV node | high metastatic | lymph |
| Teratocarcinoma, T-9 node | low metastatic | lymph |
| Colon Adenocarcinoma, Acatol | nonmetastatic | — |
| Melanoma, B-16 | low metastatic | lung |
| Lung carcinoma, RL-67 | high metastatic | lung[d] |
| Lewis lung carcinoma, LLC | high metastatic | lung |
| Murine lung carcinoma cell Line 1: | | |
| Grown without DMSO | high metastatic | |
| Grown with 3% DMSO | nonmetastatic | |

[a]PCC4$_e$-B, PCC4$_e$-P, and PCC4$_e$-107 are cell lines derived from PCC4-Blangy, PCC4-Pasteur, and PCC4-107 teratocarcinomas.
[b]Low metastatic indicates 20% of injected mice give rise to solitary metastases.
[c]High metastatic indicates 100% of multiple metastases in target organs.
[d]Metastases in other organs.

3. Rat Tumors and Rat Tumor Cell Lines

An established epithelial cell line, FRTL5, was derived from a culture of rat thyroid cells and is not tumorigenic. In accordance with the present invention, two tumorigenic but non-metastatic derivatives of FRTL5 cells, ELCL$_1$ and TRCL$_1$, have also been isolated. The properties of these non-metastatic cell lines are further elaborated upon in Table 2 and in Example 3.

The IR6 tumor is a radiation induced, transplantable anaplastic thyroid carcinoma, of epithelial origin. It is a poorly differentiated, highly aggressive adenocarcinoma which is highly metastatic. IR4 is another transplantable, radiation induced thyroid tumor which is moderately differentiated and has low metastatic potential. The properties of these tumors are further elaborated on in Example 3 and in Table 2.

4. Nucleic Acid Purification and Analysis

Tumor cells were cultivated and prepared for subcutaneous injection into mice as described under the metastatic activity subsection of this section. Injected mice were examined weekly for the appearance of tumors. Tumors were excised and used for DNA and RNA preparations. Total DNA was prepared from cells according to Sambrook et al. (Molecular Cloning: A Laboratory Manual. Cold Spring Harbor, Vol. 2, Laboratory Press, 1989. Pages 9.1–9.62).

RNAs were prepared from different tumor cells and normal cells according to the procedure described by Chomczynski et al. (1987, Anal. Biochem. 162: 156–159) or Sambrook et al. (Molecular Cloning: A Laboratory Manual, Vol. 1, Cold Spring Harbor Press, 1989:7.1–7.87). Gel electrophoresis of RNA, RNA blotting to nylon membrane filters, and hybridization with nick-translated DNA probes was as described in Grigorian et al. (1985, EMBO J. 4: 2209–2215).

Southern blots were performed using 10 μg of genomic DNA extracted from mouse liver, CSML-100 cells, human placenta and liver, rat liver, pig liver, and chicken liver. DNAs were digested with BamHI, EcoRI, and PstI endonucleases. Following electrophoresis in a 0.8% agarose gel, the DNA was transferred onto a nylon membrane (Hybond N, Amersham). The filter was prehybridized and hybridized following the standard procedure of Sambrook et al., supra.

EXAMPLE 2

Development of Benign and Metastatic Mouse Tumor Cell Lines

CSML-0, CSML-50 and CSML-100 are tumor lines established from spontaneous mammary adenocarcinomas of A/Sn mice. CSML-0 was derived from a tumor maintained by intramuscular passages and was characterized as having a low metastatic potential. Solitary lung metastases were detected in less than 10% of autopsied animals that had been killed because of a moribund condition. A second, highly metastatic subline, CSML-100, was developed by selecting for a metastatic phenotype in successive transplantations (via successive subcutaneous tail injections) of initially rare, and subsequently more frequent, CSML metastatic tumor cells. The frequency of metastasis to the lung by CSML-100 cells was 100%, by any route of primary inoculation. CSML-50 represents a cell line with an intermediate level of metastatic potential which was developed during the establishment of CSML-100. The frequency of lung metastasis by CSML-50 cells was about 50%.

The CSML-100 tumor line also caused tumors to form in A/J mice (Jackson laboratories) which have a similar genotype to that of A/Sn mice. CSML cells were not rejected by A/J mice and metastases were detected in lungs and other organs by any injection route.

A/J mice intravenously injected with CSML-100 developed tumors within 6–7 days of injection. Even when only 1×10$^4$ CSML-100 cells were injected, abundant metastases were found in lungs by 15 days post-injection (FIG. 9c). A/J mice injected with CSML-100 cells by the subcutaneous route had approximately 250 spontaneous metastases per lung 4–6 weeks later (FIG. 9d). Mice injected with CSML-0 by either route of injection had only 10–25 tumors per lung (FIG. 9a and 9b). After sacrifice of each mouse, the ovaries, liver, kidney, gonads, muscle, and brain tissues were preserved for immunohistochemical analysis. Such analysis indicated mts-1 was highly expressed in metastasized tumors, particularly in the ovarian and lung tumors.

EXAMPLE 3

Development of Benign and Metastatic Rat Tumors and Rat Tumor Cell Lines

A number of rat thyroid carcinomas and cell lines have been developed in conjunction with the present invention, by irradiating normal Fischer 344 rat thyroid cell suspensions before transplantation into the rat. Grafts of non-irradiated, monodispersed rat thyroid cells develop into morphologically and functionally normal thyroid tissue within a short time after transplantation into Fischer 344 syngeneic rats, if the level of thyroid stimulating hormone (TSH) within the rat is elevated by injection of TSH. If thyroid cells are irradiated before transplantation, thyroid carcinomas develop. The IR6 tumor was obtained as a radiation induced, transplantable anaplastic thyroid carcinoma of epithelial origin. IR6 was found to be poorly differentiated, highly metastatic and did not require TSH for growth. The IR4 tumor was also obtained as a radiation induced rat thyroid carcinoma but IR4 is moderately differentiated into a follicular carcinoma, grows slowly only when TSH is provided and has low metastatic potential. IR6CL$_1$ is a cell line derived from the IR6 tumor which retains the original properties of the parent IR6 tumor, e.g., it grows independently of TSH, is poorly differentiated and is highly metastatic.

An established epithelial cell line, FRTL5, derived from a culture of rat thyroid cells was also obtained. FRTL5 cells requires TSH and remains highly differentiated, but produces no tumors when injected subcutaneously into syngeneic Fischer 344 rats. Two tumorigenic derivatives of the FRTL5 cell line, ELCL$_1$ and TRCL$_1$, have also been isolated and characterized. ELCL$_1$ was obtained as a spontaneous mutant of FRTL5, and subsequently established as a transformed cell line which required low levels of TSH for growth. ELCL$_1$ formed primary tumors upon subcutaneous injection in syngenic rats but no metastasis was observed. TRCL$_1$ was a radiation induced mutant of FRTL$_5$ which was then established as a transformed cell line with no TSH requirement for growth. TRCL$_1$ cells produced fast-growing primary tumors with little or no potential for metastasis.

Some of the properties of the above described tumors and cell lines are summarized in Table 2.

TABLE 2

Metastatic Potential of Rat Tumors and Rat Tumor Cell Lines

| Tumors and Cell Lines | Spontaneous Metastases | Target Organs |
| --- | --- | --- |
| Thyroid carcinoma | | |
| IR6 tumor | high metastatic | Lung, |
| IR4 tumor | low metastatic | Liver, Kidney |
| Thyroid cell line | | |
| FRTL5 (non-tumorigenic) | nonmetastatic | |
| ELCL$_1$ (tumorigenic) | nonmetastatic | |
| TRCL$_1$ (tumorigenic) | nonmetastatic | |

EXAMPLE 4

Isolation of the Murine mts-1 Gene mRNA from CSML-100 and CSML-0 cell lines was prepared as described by Chomczynski et al. supra, and polyadenylated mRNA was selected as in Sambrook et al. (Molecular Cloning: A Laboratory Manual, Vol. 1, Cold Spring Harbor Laboratory Press, 1989. Pages 7.1–7.29). 2 µg poly (A)$^+$ mRNA from highly metastatic CMSL-100 cells was treated with reverse transcriptase under conditions appropriate to generate a single stranded complementary DNA (cDNA) (Sambrook et al., supra, Vol. 2. Pages 8.1–8.86). This CMSL-100 cDNA pool was subjected to subtractive hybridization with 50 µg poly (A)$^+$ mRNA from low metastatic potential CMSL-0 cells to remove cDNA's with no role in the development of metastasis. The cDNA/RNA mixture was heated at 100° C. for 5 min., cooled on ice and placed in a final reaction volume of 1 ml in 7% phenol (adjusted to pH 7.6 with 0.1M Tris-HCl, 1.25M NaCl, 120 mM sodium phosphate buffer, pH6.8) in a 10 ml glass centrifuge tube in. The tube was shaken for 7 days at 25° C. After hybridization, the mixture was extracted twice with chloroform, dialyzed against 10 mM Tris-HCl (pH 7.5), 1 mM EDTA to remove excess salts, and then precipitated with ethanol. Double stranded cDNA/mRNA, representing functions which are not unique to the metastatic phenotype, were removed by passage through a hydroxyapatite column. The single stranded cDNA was made double stranded and cloned into a λgt10 vector by standard procedures (Sambrook et al., supra pages 8.1–8.86).

Functions expressed highly during metastasis were detected by differential hybridization with CSML-100 and CSML-0 P-labeled cDNA probes. Mouse mts-1 cDNA clones were identified as strongly hybridizing with the DCSM-100 probe but weakly hybridizing with the CSML-0 probe.

EXAMPLE 5

Isolation of a Rat mts-1 cDNA

Rat cDNA libraries were prepared from normal thyroid and radiation induced thyroid carcinoma tissues as well as cell lines derived from normal and carcinogenic thyroid tumor cells. Poly (A)$^+$ mRNA was purified from highly metastatic IR6 tumors and from low metastatic potential IR4 tumors. Single-stranded cDNA was synthesized from IR6 poly (A)$^+$ RNA and the IR6 mRNA was hydrolyzed. This IR6 cDNA pool was subjected to subtractive hybridization with a 50-fold excess of IR-4 poly (A)$^+$ mRNA according to the phenol emulsion reassociation technique (PERT method) of Kohne et al. (1977, Biochemistry 16: 5329–5341). Single stranded cDNA, representing functions likely to be involved in the metastatic phenotype, was isolated from the subtractive hybridization mixture by passage through a hydroxyapatite column (which will bind double stranded nucleic acids, i.e. the RNA:DNA hybrids representing the IR6 functions of low metastatic potential) followed by alkaline hydrolysis of the remaining IR4 mRNA. The single-stranded cDNA pool was made double stranded and cloned into a λgt10 cloning vector.

The subtracted IR6 cDNA library was screened differentially with $^{32}$P-labeled single stranded cDNA probes generated by treatment of IR6 and IR4 poly (A)$^+$ mRNA with reverse transcriptase. mts-1 clones were identified by strong hybridization with the IR6 probe but weak hybridization with the IR-4 probe.

EXAMPLE 6

Isolation of the Human mts-1 cDNA

A human cDNA library was constructed in λgt10 using poly (A)$^+$ RNA prepared from HeLa cells. The library was screened with a $^{32}$P-labelled mouse mts-1 cDNA probe at 42° in 50% formamide. Filters were washed in 2×SSC with 0.1%. SDS at room temperature and then twice in 0.2×SSC with 0.1% SDS at 50° C. Strongly hybridizing cDNA clones were sequenced; the human mts-1 cDNA was identified by high sequence similarity to the mouse mts-1 cDNA in regions outside the highly conserved Ca$^{++}$ binding domain. This human mts-1 clone is full length as judged by sequencing of the human genomic mts-1 gene and by primer extension analysis of mts-1 mRNA using mts-1 oligonucleotide probes. The nucleotide and amino acid sequences of the human mts-1 gene are provided as SEQ ID NO:1 and 2, and also given in FIG. 1 and 2.

The mts-1 cDNA was also isolated from human melanoma cell line Wm64 by reverse transcription of mRNA isolated from those cells followed by polymerase chain reaction.

Reverse Transcriptase Polymerase Chain Reaction (RT-PCR)

Total RNA from human melanoma cell line Wm64 was pretreated with RNase free DNase I (1U/µl) in 2 mM $MgCl_2$ for 30 minutes at 37° C. then 95° C. for 5 minutes to inactivate the DNase; poly $A^+$ RNA was not routinely treated with DNase I before an RT-PCR experiment. RNA (1 µg total RNA or 50 ng poly $A^+$ RNA) was reverse transcribed in the presence of 50 mM Tris-HCl pH 8.3, 75 mM KCl, 3 mM $MgCl_2$, 3 µM oligo-$dT_{15}$, 0.3 mM each dNTP, 200U M-MLV reverse transcriptase at 22° C. for 10 minutes, 42° C. for one hour and 90° C. for 10 minutes. The following human mts-1 primers were used for synthesis of the human mts-1 cDNA by PCR reaction:

5'ATG GCG TGC CCT CTG GAG AAG-3' (SEQ ID NO:8)

5'TTT CTT CCT GGG CTG CTT ATG-3' (SEQ ID NO:9).

PCR amplification was done in 10 mM Tris HCl (pH 8.4), 50 mM KCl, 1.5 mM $MgCl_2$, 0.01% gelatin with 2.5 mM dNTP, 0.6 µM each primer and 1.25U Taq DNA polymerase. Amplification was by 35 cycles of: 94° C. for 1 min; 52° C. for 2 min; 72° C. for 3 min, followed by a 7 min extension period at 72° C.

Amplified DNA was isolated from a 1% agarose gel an cloned into a baculovirus transfer vector as described in Example 7.

EXAMPLE 7

Expression of the mts-1 Gene Product

Overexpression of the mts gene product, is accomplished by DNA transfections using the vector system described by Lockshon and Weintraub. This vector is a pUC19 based vector system, very similar to the Bluescript™ vector (FIG. 3). In the unique HindIII site of the Bluescript™ vector, a eukaryotic control element harboring a strong murine sarcoma virus promoter, followed by a unique EcoRI site, followed by SV40 polyadenylation sequences is introduced. The complete mts-1 cDNA is introduced into the unique EcoRI site downstream from the MSV-LTR sequences. Because of the presence of an internal EcoRI site in the mts-1 cDNA, partial EcoRI digestion of the mts-1 recombinant is done to isolate the entire mts-1 cDNA molecule. Retroviral promoters with LTRs are very strong and overexpression of the mts transcript is expected. The mts-1 recombinant expression vector can be used for both permanent or transient expression. However, stable (permanent) transfectants are desirable because stable transfectants can be clonally purified, and represent a homogeneous population of a given phenotype useful for quantitating metastatic potential.

Expression of mts-1 protein from a pTrcHisB vector

Large quantities of the mts-1 specific protein were expressed using the inducible bacterial vector pTrcHisB (Invitrogen) (FIG. 10a). Murine mts-1 cDNA was subcloned in frame (confirmed by sequence analysis) into a BamHI-KpnI site with the multiple cloning site of pTrcHisB. This generated plasmid pTBM1. The fusion protein expressed by pTBM1 had 6 tandem histidine residues (which have a high affinity for a $Ni^{++}$ charged resin), an enterokinase specific cleavage site, and the mts-1 protein product. Expression of the fusion protein encoded by pTBM1 was induced by IPTG. Similar constructs were generated with human mts-1 cDNA.

Expression of mts-1 protein in a baculovirus expression vector

A plasmid containing the cytomegalovirus promotor was used to construct pCMV/mts-$1_H$ or pCMV/mts-$1_m$ high expression vectors harboring mts-1 human and murine cDNAs, respectively.

The baculovirus expression vector mts-1-BacPAK$_6$ plasmid was constructed from the pCMV clones as follows. pCMV-mts-1 was digested with BamH1, and the mts-1 cDNA fragment was purified from a 1% agarose gel. The purified fragment was ligated into BamH1-cleaved pBacPAK1 and the ligation mix was transformed into *E. coli* JM109 cells. Positive clones were identified and plasmid DNA was sequenced to confirm the orientation and integrity of the ligation junction.

Transfer vector pBacPAK-mts-1 was transfected into Sf21 cells, along with Bsu361 digested BacPAK6 viral DNA. Soon after infection, the cells were overlayered with 1% agarose to visualize the plaques and to prevent mixing of clones. After 4–5 days of infection, the cells were stained with neutral red which is taken up by healthy cells, but not by the dead cells. Plaques appeared as clear circles against red or pink background.

Western Blot analysis using the α-mts-1 antibody was conducted to confirm that several mts-1 recombinant viruses produced mts-1 proteins.

EXAMPLE 8

Purification of mts-1 Protein

Purification of the mts-1 protein parallels that of other S100 family members which have been purified to homogeneity from bovine brain (Baudler, et al. J. Biol. Chem. 261: 8204–8212, 1986). Exceedingly high degrees of purification can be achieved because of the stability of the protein and the availability of several affinity chromatography steps including phenothiazine-agarose, zinc dependent binding to phenyl sepharose. FPLC chromatography on Mono Q is known to separate S100 family members and other HPLC columns have been developed such as melittin silica, to affinity purify S100 proteins. Tissues or cells providing large amounts of mts-1 include not only the bacterial, yeast and mammalian cell lines engineered to express large quantities of recombinant mts-1, but also the highly metastatic tumors and cell lines shown to express mts-1 by the present invention.

Purification of His-mts-1 Fusion

Figure 10B:
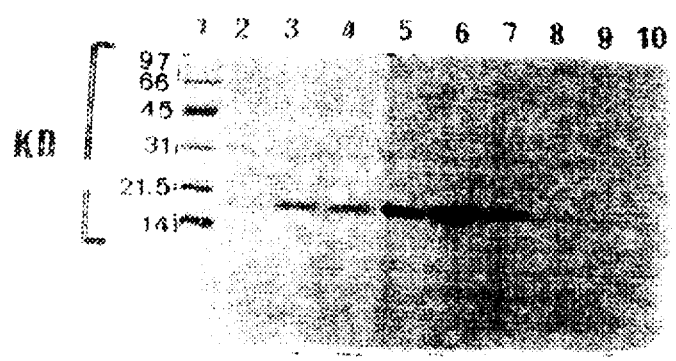
FIG. 10b depicts a Coomassie Brilliant Blue-stained gel illustrating the profile of proteins eluted from a Ni$_{++}$-NTA column used to purify mts-1 protein expressed by cells containing pTBM1. Elution was with a series of buffers having pH values varying from 5.9 to 4.5. A single major protein, the mts-1 protein, is eluted.

An overnight culture transformed with pTBM1 was diluted 1:100 and allowed to grow 1.5 hours (until $OD_{600}$= 0.3). The culture was then induced with 1 mM IPTG and allowed to grow 4.5 hours more at 37° C. Cells were harvested, cell pellets were then collected by centrifugation and resuspended in a 6M guanidinium-HCl buffer. The cells were stirred for 1 hour and then centrifuged at 18K rpm for 15 min at 4° C. The supernatant was collected and added to a 50% slurry of $Ni^{++}$-NTA resin (obtained from Qiagen). The mixture was stirred for an hour and loaded onto a column. The column was washed in a series of urea based buffers which differed only in pH (each wash being of a lower pH). The protein was eluted in 3 ml fractions using buffer D (8M urea, 0.1M Na Phosphate, 0.01M Tris/HCl, pH 5.9). A large amount of the protein did not elute until the pH of the buffer was lowered to 4.5 (buffer E): monomeric forms of the histidine fusion eluted in buffer D, whereas aggregates eluted in buffer E. Aliquots of each fraction were boiled in SDS-PAGE loading buffer and loaded onto 12% SDS-polyacrylamide gels. The gels were stained with Coomassie Brilliant Blue. The results of such experiments are depicted in FIG. 10b. After the purity of the His-Mts1 fusion protein was confirmed, assays were performed to determine relative protein concentrations. Fractions D2 and E1 (which contained approximately 3.2 mgs protein total) were pooled and run on another SDS-polyacrylamide gel. Strips were cut out from the gel and stained in Coomassie Brilliant Blue to determine the location of the His-Mts1 protein in the gel. The portion of the gel containing the His-Mts1 fusion was cut out and the protein was isolated from the gel by elution.

EXAMPLE 9

Generation of Polyclonal Antibodies
Antibodies Against mts-1 Peptides
Synthetic oligopeptides with the following amino acid sequences were made:

1) Human mts-1 amino acids 2–11 (unique):
   Ala-Cys-Pro-Leu-Glu-Lys-Ala-Leu-Asp-Val
2) Human mts-1 amino acids 22–37 (the calcium binding domain):
   Lys-Glu-Gly-Asp-Lys-Phe-Lys-Leu-Asn-Lys-Ser-Glu-Leu-Lys Glu-Leu
3) Human mts-1 amino acids 42–54 (unique):
   Leu-Pro-Ser-Phe-Leu-Gly-Lys-Arg-Thr-Asp-Glu-Ala-Ala
4) Human mts-1 amino acids 87–101 (unique):
   Asn-Glu-Phe-Phe-Glu-Gly-Phe-Pro-Asp-Lys-Gln-Pro-Arg-Lys-Lys Peptides 1, 3 and 4 were chosen as mts-1 antigens because they encode unique proteins of the mts-1 protein, i.e. these regions of the mts-1 protein do not share homology with other proteins, in particular with other calcium binding proteins. Peptide 2 was chosen because it encodes the calcium binding domain of mts-1. Therefore, peptide 2 generates antibodies reactive with many members of the calcium binding protein family.

New Zealand white female rabbits were immunized by subdermal injection with 100 µl of Freund's complete adjuvant containing 0.1–1 mg of oligopeptide in 10 locations along the back. The rabbits were first shaved on both sides of the back for easy subdermal injection. The antigen-adjuvant mixture was prepared by mixing in two connected 1 ml glass tephlon syringes. Typically rabbits are then injected with abut 1 mg of antigen at each 2 month interval following the primary injection, until the serum is positive at a dilution of greater than $10^{-4}$ when assayed by immunoblotting.

Antibodies Against Whole mts-1 Protein

The mts-1 protein was expressed as a His-Mts1 protein (Examples 7 and 8). Host cell lysates containing the His-Mts1 protein were fractionated over a $Ni^{++}$-NTA column (Qiagen). Fractions containing the most His-Mts1 protein were pooled and electrophoresed on an SDS-polyacrylamide gel. The purified protein was eluted from the gel and sequenced to confirm that it was His-Mts1.

Three chickens were then immunized with the purified His-Mts1 protein. Chickens were chosen for two reasons. First, mts-1 is highly conserved in mammals and an avian system was expected to provide a better immune response. Second, antibodies can easily be obtained from the eggs of the chickens. Continuous bleeding of the animal to obtain antibodies is, therefore, avoided.

Figure 13:
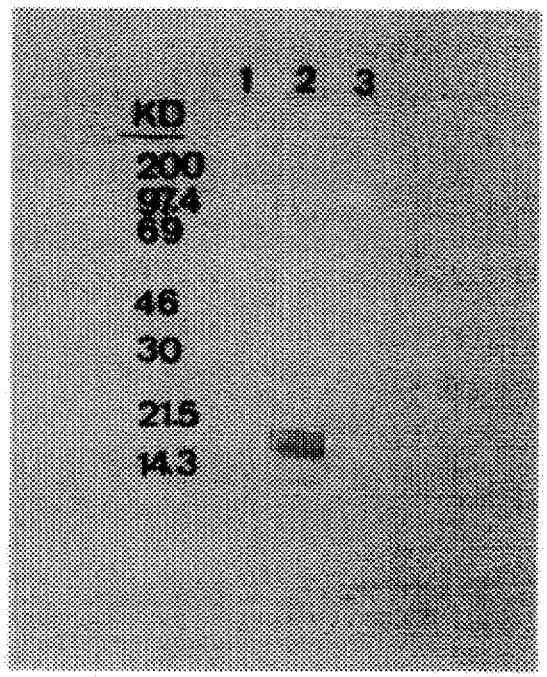
FIG. 13 depicts a western blot of CSML-0 (Lane 1) and CSML-100 (Lanes 2 and 3) cell lysates. Lanes 1 and 2 were probed with the chicken anti-mts-1 antibody (α-mts-1) using a secondary antibody (rabbit anti-chicken IgG-HRP) for detection. Lane 3 was similarly probed except that free mts-1 protein was added during the incubation with the α-mts-1 antibody. An approximate 10–12 kd mts-1 protein is detected only in CSML-100 cells and only when no free mts-1 protein is present to compete for binding to the α-mts-1 antibody. Therefore, the α-mts-1 antibody is highly specific for mts-1 protein.
Figure 14A:
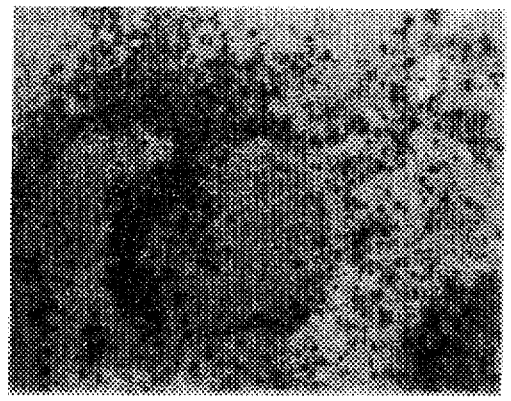
FIG. 14a depicts a frozen mouse spleen section probed with the α-mts-1 antibody. Rabbit anti-chicken IgG-HRP was used for detection of the mts-1 antigen-antigen antigen complex (dark spots).

The polyclonal antibody generated was named α-mts-1, and its efficacy on Western blots and tissues was established (see Example 16 and FIGS. 13 and 14).

EXAMPLE 10

Monoclonal Antibody Production

Monoclonal antibodies are prepared in accordance with the techniques developed by Kohler and Mulskin (Eur. J. Immunol. 6:511–519, 1976) and Harlow et al. (Antibodies: A Laboratory Manual, Cold Spring Harbor Laboratory Press, 1988). Balb/c mice are immunized subdermally with 100 ul of Freund's complete adjuvant containing 0.1–1 mg of the conjugated or non-conjugated mts-1 oligopeptdies described in Example 9. Two weeks after the initial injection, the mice are boosted with the appropriate mts-1 antigen by intravenous and intraperitoneal injection of 100 ug of antigen in phosphate buffered saline (PBS).

Five days after the last injection and after confirmation of the presence of antibody in mouse sera, the mice are sacrificed and their spleens removed. Spleen cells are obtained by gentle disruption of the spleen in a 7 ml Dounce homogenizer in 3.5–4 ml PBS. The cells are then pelleted at 1200 rpm in a PR6 centrifuge for 6 minutes at room temperature. The supernatant is removed into a suction flask, and the cells are resuspended in 15 ml 0.83% $NH_4Cl$. This suspension is incubated at room temperature for 5 minutes then underlain with 10 ml fetal calf serum at 37° C. The cells are again pelleted by centrifugation for 8 minutes, at 1200 rpm at room temperature, then the supernatant is withdrawn into a suction flask cells resuspended in 20 ml PBS.

The following solutions are prepared for use in the subsequent cell fusion:

Hypoxanthine (H), 680 mg/100 ml $H_2O$; add 204 drops conc. $H_2SO_4$y; heat to dissolve
Aminopterin (A), 46.4 mg/100 ml $H_2O$; add 2 drops 1.0N NaOH to dissolve
Thymidine (T), 775 mg/100 ml $H_2O$; add 45 mg glycine
PEG-DME—melt PEG at 42° C., then add 1 ml DME (at 37° C.); adjust pH with 1.0N NaOH to 7.6
DMEM—to 500 ml DME add 37.5 ml a- horse serum; 37.5 ml FCS, 10.0 ml L-glutamine, 0.2 ml garamycin
2× HAT-DME—to 200 ml DME add 25.0 ml a- horse serum, 25.0 ml FCS, 4.0 ml L-glutamine, 0.2 ml garamycin, 0.8 ml H, and 0.8 ml A, and 0.8 ml T (2× HT-DME omits A)
Cloning Agar—350 mg unwashed Difco agar in 25 ml $H_2O$, autoclaved
Cloning Medium—to 25 ml 2× DME, add 35 ml filtered, condition DMEM, 7 ml a- horse serum, 7 ml FCS, 1 ml L-glutamine, 0.1 ml garamycin.

Two 30 ml flasks of plasmacytoma P3 NS1/1-Ag4-1 cells are added to centrifuge tubes and spun down at 1200 rpm for 8 minutes at room temperature. The spleen cells are resuspended in 20 ml PBS. From each suspension, 0.01 ml is removed and added to 0.1 ml 0.4% trypan blue and 0.3 ml PBS and the cells counted. The volume of each suspension is adjusted so as to obtain a spleen cell to NS1/1-Ag4-1 cell ratio of 10:1, and the suspensions are then mixed. The mixture is pelleted at 1200 rpm for 8 minutes at room temperature and all but about 0.1 ml of supernatant removed. The cells are then resuspended in the remaining liquid and then added to 1.3 ml of 1:1 PEG-DME solution, pH 7.6. Every minute the volume of the solution is doubled with DME until the final volume is 25 ml.

The cells are again pelleted, the supernatant decanted, and the cells resuspended in enough 50% 2× HAT-DME/50% conditioned DMEM (the supernatant retained form the Sp2/0 cells above) to yield a final concentration of about $3.5 \times 10^6$ spleen cells. The cells are distributed into a 96-well flat-bottom microtiter plate (TC-96; Flow Laboratories), at 0.1 ml/well. The plate is incubated at 37° C. in humidified air/$CO_2$ until visible colonies appear, usually about 10–12 days. The contents of the well is transferred to 0.5 ml of HAT-DME/conditioned DME in a TC-24 plate (Flow Laboratories). When healthy cell growth appears (about 2–5 days), about 0.35 ml medium is removed and tested for antibody production by enzyme-linked immunosorbent assay (ELISA), hemagglutinin inhibition assay, or neuraminidase inhibition assay. When those cells producing the antibodies of interest are growing well, one drop for each culture is transferred into 1.0 ml DMEM in a TC-24.

To clone the hybrid cells, 25 ml of melted agar and 76 ml of cloning medium is combined, and 5 ml is pipetted into 60 mm petri dished and left to solidify. Cells from DMEM cultures are diluted in 50% DMEM/50% conditioned DMEM, $10^{-1}$ or $10^2$ depending on cell growth. Into sterile tubes is placed 0.1 ml of each of the two dilutions, and to each is added 0.9 ml of cloning medium/agar mixture. This is mixed well and poured over the surface of the agar underlay. After solidification the plates are incubated at 37° C. incubator until colonies are visible with the naked eye, typically about 7–10 days. Colonies are then picked and transferred 0.1 ml of DMEM/conditioned DMEM in a TC-99 plate and incubated at 37° C. in a $CO_2$ incubator. After the culture is acidic (usually 1–4 days), transfer is made to 0.05 ml DMEM in TC-24 plate. When the growth is 50% confluent, the medium is removed and tested for antibody production are previously. Those clones producing mts-1 specific antibodies are moved into 5 ml DMEM in 25 cm² flasks. Cloned cells are then frozen or injected into mice for ascites production.

EXAMPLE 11

Sandwich Assay For mts-1

For detection of the presence of mts-1 in serum or cleared cell lysates of tissue specimens, approximately 100 ul of a monoclonal antibody prepared as in Example 9 or 10 is immobilized on latex beads and is contacted with about 100 ul of the serum or cleared lysate to be tested. The immobilized antibody and lysate are allowed to react for a period of about ten minutes and then the latex beads with the mts-1 antigen bound to the immobilized antibody are rinsed with a solution of PBS (phosphate buffered saline). To the latex beads is then added about 100 ul of mts-1 specific antibody conjugated to horseradish peroxidase. The labeled antibody bead mixture is incubated for a period of about ten minutes. At this time, an enzyme substrate, hydrogen peroxide and aminoantipyrine, are contacted with the beads, and this mixture is incubated for a period of about 5–10 minutes, at which time the development of color in the sample is an indication of a positive reaction and the presence of mts-1.

EXAMPLE 12

Expression of mts-1 is 10–100 Fold Higher in Metastatic Tumor Cells Than in Non-Metastatic Cells To examine the expression levels of mts-1, mRNA was purified from metastatic and benign tumors, and cell lines derived from such tumors, as well as from corresponding normal tissues. Purified RNA was size fractionated in a gel and blotted onto nylon membranes for Northern analysis with mts-1 nucleic acid probes.

Figure 4:
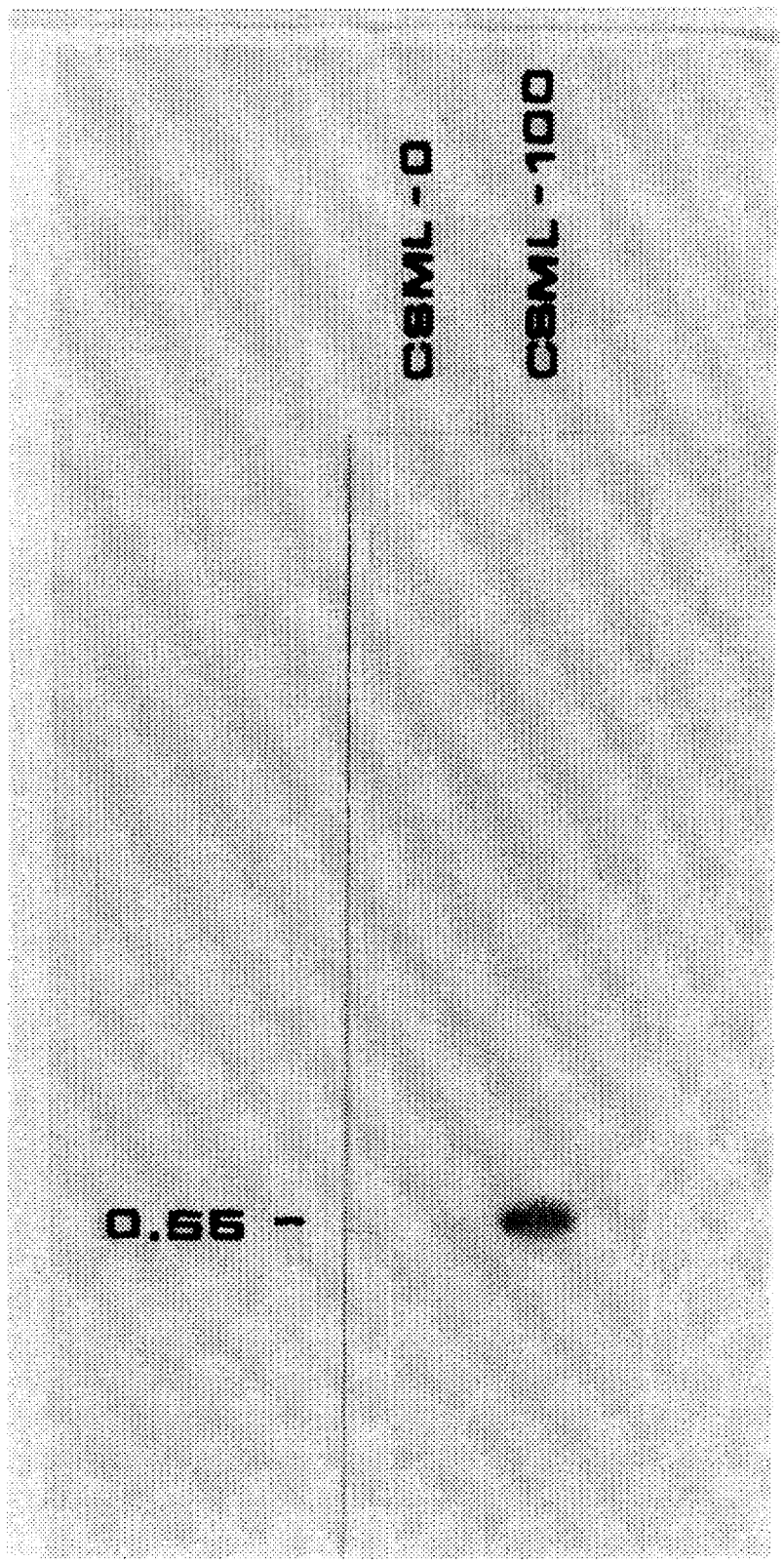
FIG. 4 illustrates an autoradiograph showing detection of the mts-1 transcript by a mts-1 nucleic acid probe in a Northern blot of mRNA from a cell line with low metastatic potential (CSML-0) and a cell line with very high metastatic potential (CSML-100).

FIG. 4 shows that the CSML-0 cell line of the present invention, which has a very low metastatic potential, had very low, or non-detectable levels of the mouse mts-1 transcript. In contrast, the CSML-100 cell line of the present invention, which has an extremely high metastatic potential, expressed high levels of mts-1. It is estimated that metastatic CSML-100 cells express at least 100-fold more mts-1 than do non-metastatic CSML-0 cells.

Figure 5:
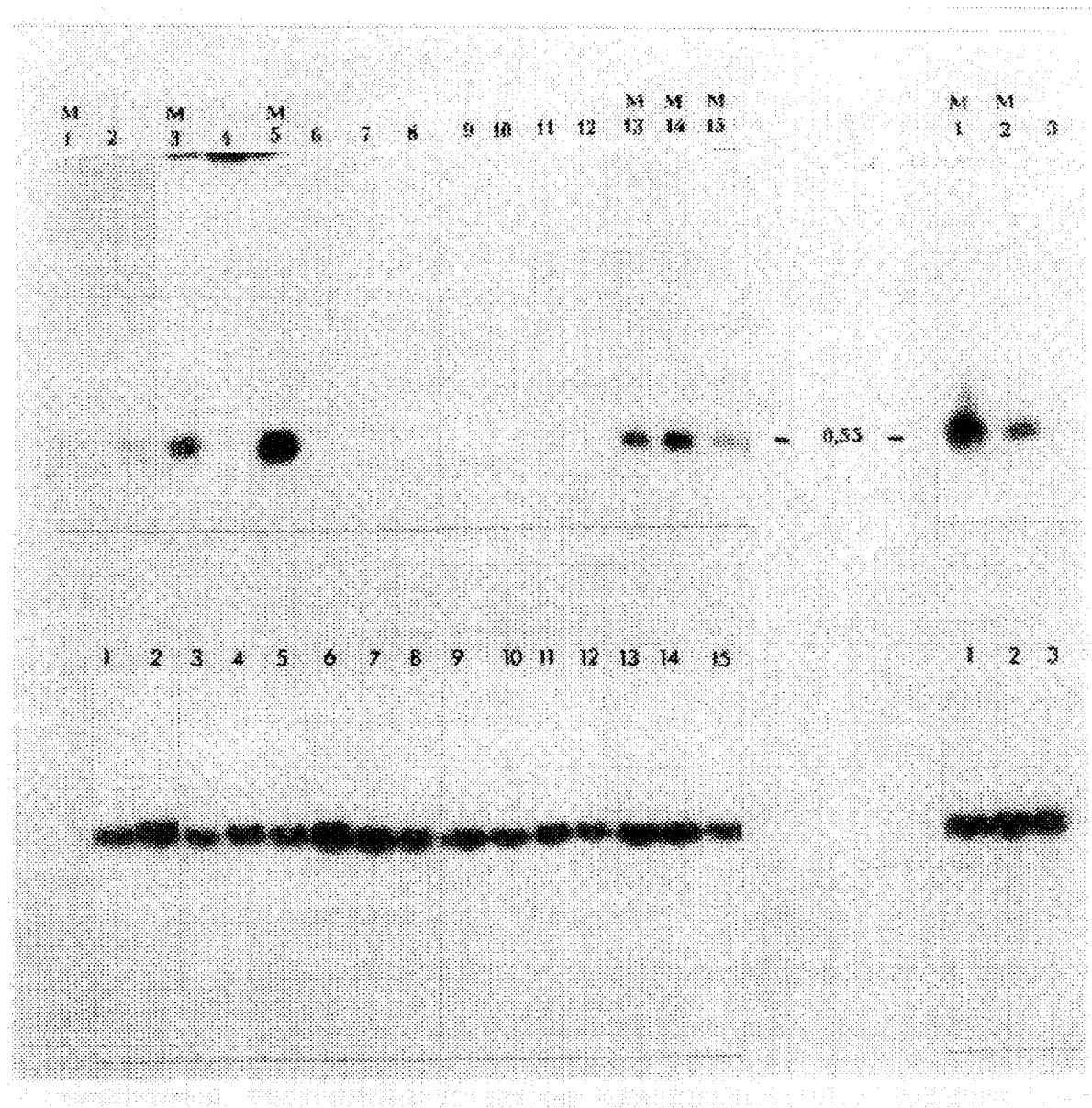
FIG. 5 illustrates an autoradiograph showing detection of the mts-1 transcript by a mts-1 nucleic acid probe in a Northern blot of mRNA from different metastatic (depicted with an "M" above the lane) and non-metastatic mouse tumors and cell lines. In the top autoradiograph: Lane 1-HMC-Lr; Lane 2-HMC-0; Lane 3-RL-67; Lane 4-B-16, Lane 5-LLC; Lane 6-Acatol; Lane 7-C12; Lane 8-PCC4c-B; Lane 9-PCC4c-P, Lane 10-PCC4c-107; Lane 11-PCC4107; Lane 12-T9; Lane 13-LMEC; Lane 14-T36; Lane 15-T36cL. The bottom autoradiograph depicts the same Northern blot hybridized with an actin probe, providing a comparison of the amounts of mRNA in each lane.

Similarly, in a separate experiment, various metastatic and non-metastatic tumors and tumor cell lines were tested for their mts-1 expression levels, by Northern analysis using a $^{32}$P-labeled mouse mts-1 probe. The properties of these tumors and cell lines are described in detail in Examples 1, 2 and 3 and in Tables 1 and 2. As shown in FIG. 5, only those tumors and cell lines which are metastatic (indicated by an "M" above the gel lane) exhibit high levels of mts-1 expression. Metastatic cell types exhibiting increased mts-1 expression include: RL-67 lung carcinoma tumors, Lewis Lung carcinoma tumors, LMEC embryo-carcinoma tumors, and T-36 embryo-carcinoma tumors and cell lines.

Figure 6:
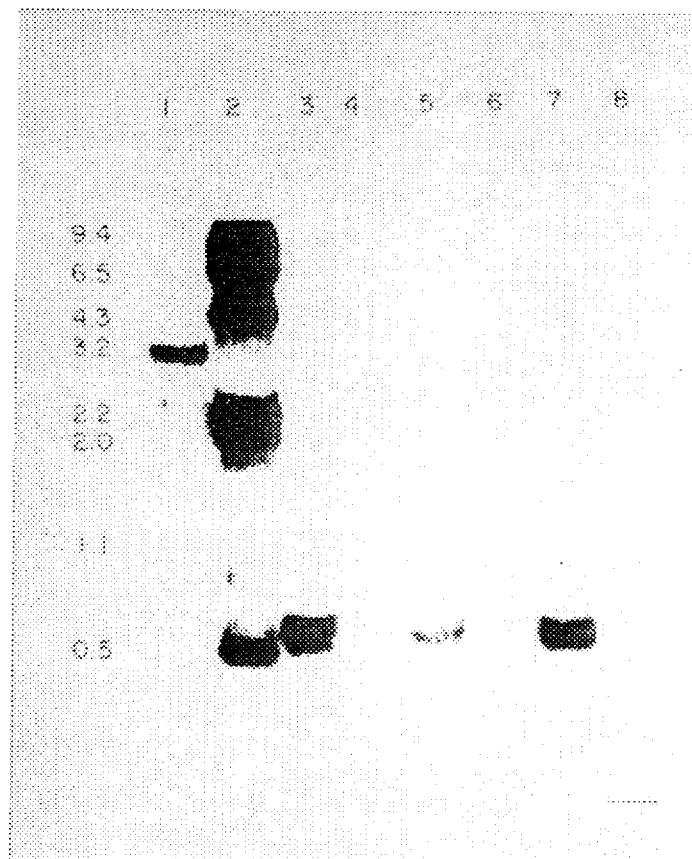
FIG. 6 illustrates an autoradiograph showing detection of the mts-1 transcript by a mts-1 nucleic acid probe in a Northern blot of mRNA from various tumors and tumor cell lines. Lanes 1 and 2-size markers; Lane 3-mouse lung carcinoma Line 1 grown without DMSO; Lane 4-mouse lung carcinoma Line 1 grown with 3% DMSO; Lane 5-IR6 tumor; Lane 6-TRCL$_1$ cell line; Lane 7-IR6 cell line (IR6CL$_1$); Lane 8-FRTL5 cell line.
Figure 7A:
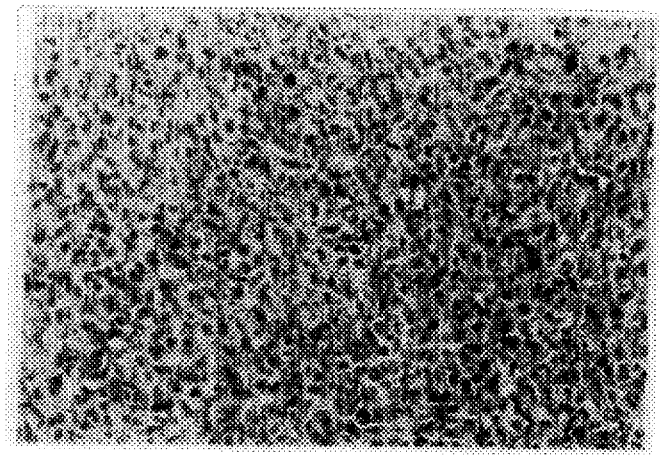
FIGS. 7a–d depicts a histopathological characterization of some of the rat tumors of the present invention, demonstrating the morphological and histological identity of these tumors with corresponding human tumors.
Figure 7B:
Figure 7C:
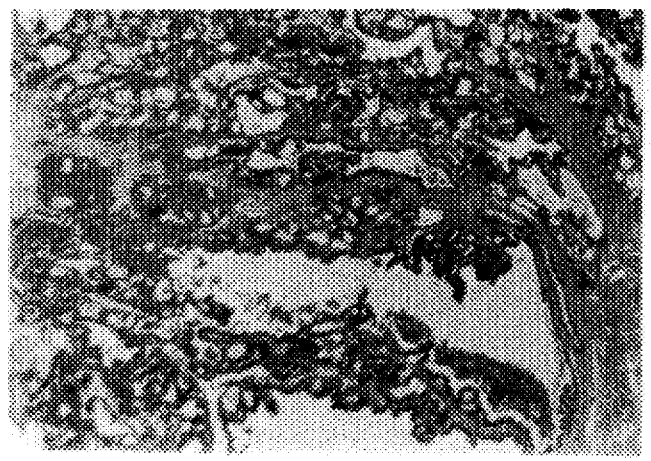
Figure 7D:
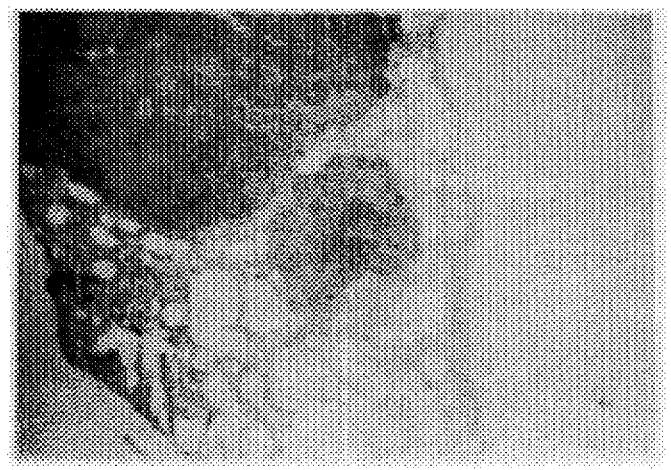

FIG. 6 shows that the highly metastatic adenocarcinoma rat tumor, IR6 (lane 5), and a cell line derived from IR6 (lane 7), as well as a metastatic cell line derived from a mouse lung carcinoma, Line 1 (lane 3) all exhibit 10–100 fold increased levels of mts-1 expression compared to a tumorigenic but non-metastatic cell line, $TRCL_1$ (lane 6) or a non-tumorigenic FRTL5 cell line (lane 8).

Hence these data demonstrate unequivocally that mts-1 expression is increased 10–100 fold in metastatic cells of diverse types relative to normal cells or non-metastatic (benign) tumor cells.

Table 3 further illustrates that only metastatic cells or cells with a high degree of motility express high levels of mts-1 RNA. Detection was by northern analysis using γ-actin expression for normalization. Autoradiograms were densitometrically traced, and a numerical value between 0–5 was assigned relating the tracing peak height to the amount of expression. The status of each cell type tested was characterized as normal (N), benign (B), metastatic (M) or cell line (C). The number of samples tested is indicated under the status of cell type.

Table 3 illustrates that only metastatic cell types have an mts-1 expression level greater than 0.5. Accordingly, high levels of mts-1 expression are observed in numerous metastatic cell types including, for example, liver hepatomas, lung carcinomas, pancreatic cancers, breast adenocarcinomas, endometrial cancers, ovarian cancers, cervical cancers, melanomas, lymphomas and leukemias. However, such high levels of mts-1 expression are observed only in metastatic cells, non-metastatic cells do not express high levels of mts-1.

TABLE 4

Selective Expression of mts-1 in Metastatic Cells or Cells with High Degree of Motility

| Phenotype of Tissue | No. of Samples; Status | | | | Level of Expn. |
|---|---|---|---|---|---|
| | N | B | M | C | |
| Adult Liver | 5 | — | — | — | 0 |
| Liver Adenoma | — | 5 | — | — | 0 |
| Liver Hepatoblastoma | — | 5 | — | — | 0 |

TABLE 4-continued

| | | | | | |
|---|---|---|---|---|---|
| Liver Hepatoma | — | — | 4 | — | 1.0 |
| Adult Colon | 4 | — | — | — | 0.4 |
| Colon Carcinoma | — | 5 | — | — | 0.43 |
| Adult Kidney | 2 | — | — | — | 0.1 |
| Kidney Carcinoma | — | 2 | — | — | 0.1 |
| Adult Lung | 2 | — | — | — | 0.1 |
| Small Lung Carcinoma | — | — | 2 | — | 1.0 |
| Adult Pancreas | 1 | — | — | — | 0 |
| Pancreatic Cancer | — | — | 1 | — | 1.0 |
| Normal Breast | 4 | | | | 0 |
| Breast Carcinoma | | 2 | | | 0 |
| Breast Adenosarcoma | — | — | — | 2 | 1.0 |
| Endometrial Cancer | — | — | 2 | — | 1.5 |
| Ovarian Cancer | — | — | 2 | — | 1.4 |
| Cervical Cancer | — | — | 2 | — | 1.5 |
| ASPC 1 Pancreastic Cancer | | | | 1M | 1.0 |
| AN3CA Endometrial Cancer | | | | 1M | 1.5 |
| BIX3A Ovarian Cancer | | | | 1M | 1.5 |
| Hela Cervical Cancer | | | | 1M | 1.5 |
| MCF7-1 Breast Cancer | | | | 1 | 0 |
| AS49-1 Lung Cancer | | | | 1(M) | 0.8 |
| MC1 Neuroblastoma Line | | | | 1 | 0 |
| Y79 Retinoblastoma | | | | | 0 |
| Primary Melanoma Wm278 | | | | 1 | 0.5 |
| Corel Primary Melanoma | | | | 0 | 1.0 |
| Wm8 Melanoma | | | | 1(M) | 2.0 |
| Wm164 Melanoma | | | | 1(M) | 2.0 |

Normal B Cells Do Not Express mts-1

| B-Cell Lymphoma & Leukemias | | |
|---|---|---|
| Type | No. | Level of Expn. |
| Cleaved B Cell Lymphoma | 1 | 3 |
| Hairy Cell Leukemia | 1 | 4 |
| CML Crisis B Cells | 3 | 3 |

| Leukemias | | |
|---|---|---|
| Type | No. of Samples Tested | Average mts-1 Expn. Level |
| CML (chronic probe) | 23 | 0.49 |
| CML (crisis) | 12 | 1.9 |
| CMML | 1 | 1.0 |
| ALL | 1 | 3.0 |
| AML | 6 | 0.7 |
| AMML | 2 | 1.0 |
| Pure Monocytic Leukemia | 3 | 1.5 |
| Abnormal Blood Infiltrated with High WBC Count Separated by Ficoll-Hypague Gradient | | |
| Pellet | 4 | 0.3 |
| Interface | 5 | 0.6 |

EXAMPLE 13

Introduction of the mts-1 Gene into Cultured Cells Confers a Metastatic Phenotype According to the present invention, mts-1 is not expressed in normal, or nonmetastatic tumor cell lines, from the rat thyroid or the mouse lung. However, the highly metastatic Line 1 cell line, derived from a mouse lung carcinoma, does express mts-1 mRNA. When Line 1 cells are grown in the presence of 3% DMSO, they lose their metastatic potential and also do not show detectable levels of mts-1 mRNA. These data indicated that mts-1 expression is correlated with the metastatic phenotype.

To establish that high levels of mts-1 expression can confer a metastatic phenotype the rat mts-1 cDNA was cloned into the MSV vector depicted in FIG. 3, to allow high expression of the mts-1 protein. This mts-1 expression vector was co-transfected into mouse lung carcinoma Line 1 cells with a plasmid encoding a selectable neomycin (Neo) gene. Stable cell lines resistant to neomycin were tested for integration of the mts-1 gene into their genome by Southern blot analysis of their genomic DNA. The controls for this experiment were Line 1 cells stably transfected only with the selective neomycin resistance gene grown in the presence of 3% DMSO, as well as non-transfected Line 1 cells grown without DMSO.

Figure 8:
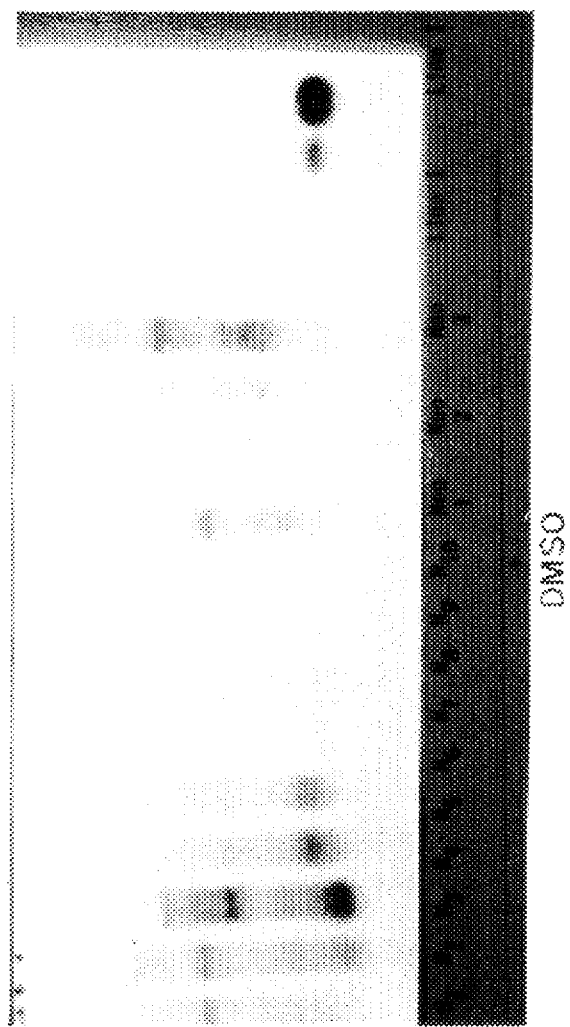
FIG. 8 illustrates an autoradiograph showing detection of the mts-1 transcript by a mts-1 nucleic acid probe in a Northern blot of mRNA from various Line 1 murine lung carcinoma cell lines containing a transfected copy of the rat mts-1 gene (N1–N10), or just an antibiotic resistance marker (Neo 1–3), all grown in the present of 3% DMSO; compared to Line 1 cells grown without DMSO (Line 1). DMSO inhibits the development of the metastatic phenotype as well as mts-1 expression in non-transfected Line 1 cells, hence transfection of mts-1 can overcome this block.

Ten transfectants (N1–N10) possessing the transfected mts-1 gene were grown in 3% DMSO to test whether acquisition of the highly expressed recombinant mts-1 gene could generate a metastatic phenotype in cells that are normally not metastatic. $10^5$ cells of transfectants N2, N3, N4, N5, and N8 were injected in the tail veins of 3 mice. As controls, $10^5$ cells of Line 1 cells, and two neomycin only transfectant cell lines (Neo 2 and Neo 3) were injected into the tail veins of 3 mice. The animals were sacrificed after 2 weeks and tested for lung metastasis after staining with India ink and fixation. The animals injected with N4 and N5 cells grown in 3% DMSO prior to injection, exhibited high levels of metastasis, equivalent to Line 1 cells grown in the absence of DMSO, while other cell lines gave rise to low levels of metastasis. The fact that not all transfected cell lines gave rise to high levels of metastasis might have been due to a variation in mts-1 expression levels caused by mts-1 insertion into "silent" regions of the genome. To examine the expression levels of mts-1 in N1–N10 transfectants grown in 3% DMSO, mRNA was extracted from these cell lines prior to injection into mice, and analyzed for mts-1 mRNA expression levels by Northern analysis. As shown in FIG. 8, not all transfectants exhibit high levels of mts-1 expression, probably because of the influence of genomic regulatory elements lying near the mts-1 insertion site. Transfectant cell lines N3, N4 and N5 have high levels of mts-1 expression, but the N3 cell line gives rise to a low molecular weight mts-1 transcript, indicating that the mts-1 gene of this transfectant cell line may be defective due to a rearrangement during transfection and integration into the genome.

Table 3 shows that similar data were obtained by intravenous injection into rats of transfectant cell lines containing expression vectors with the rat mts-1 gene in a sense and antisense orientation, relative to the MSV LTR promoter.

Hence, these data indicate that the metastatic phenotype can be generated in non-metastatic cells by the introduction of a highly expressed mts-1 gene.

TABLE 3

Mouse Lung Metastasis Counts Using Different mts-1 Transfectants

| | Neo + DMSO | Line 1 + DMSO | Line I | Clone 156/3 (N$_3$) + DMSO | Clone 156/4 (N$_4$) + DMSO | Clone 156/5 (N$_5$) + DMSO |
|---|---|---|---|---|---|---|
| Intravenous | 5 | 57 | 190 | 342 | 355 | 360 |
| Injection | 0 | 38 | 205 | 300 | 495 | 460 |
| 10$^5$ Cells | 0 | 65 | 251 | 320 | 310 | 310 |
| Into Tail Vein | 11 | 68 | 300 | 75 | 142 | 120 | rat mts-1 clone 156 = sense construct
rat mts-1 clone 162 = antisense construct

In the above experiment IR6 tumor cells alone generate lung metastasis in 20% of the injected rats, with 1–2 tumors observed in the kidneys of some rats. 50% of rats injected with transfectants containing mts-1 in a sense orientation (cell lines 156/2, 156/7 and 156/8) had metastases, while 10% of rats injected with transfectants containing mts-1 in an antisense orientation (cell lines 162/9 and 162/1) had metastases.

Hence transfection of a mammalian mts-1 gene into mice or rat cells can cause such cells to undergo metastasis when they are injected into a mouse or rat.

EXAMPLE 14

CSML-100 Cells Grow More Slowly than CSML-0 Cells

Methods

CSML-0 and CSML-100 cells were seeded at a density of $10^6$ cells/dish and counted the following day using a hemacytometer. The relative rates of DNA synthesis were measured by incorporation of $^3[H]$ thymidine. Both experiments were done in triplicate, and the data are reported as an average.

DNA synthesis was measured as follows. The cells were washed once with media. 2 mls of media containing 1 µl of $^3[H]$ thymidine was added to the cells and incubated for 4 hours. The cells were washed twice with PBS and TCA precipitated following standard protocols. The TCA precipitate was dissolved in 0.1N NaOH containing 0.5% Triton X-100 and placed on ice for 30 minutes. The resultant suspension was added to 6 mls of scintillation fluid for scintillation counting.

Results

Table 5 illustrates that less cell growth and less tritiated thymidine incorporation was observed for metastatic CSML-100 cells than for non-metastatic CSML-0 cells.

| Cell Line | $^3[H]$Thymidine Incorporation (dpm) | Cells/Dish | DNA Synthesis/Cell |
|---|---|---|---|
| CSML-0 | 6428 | $1.6 \times 10^6$ | $4.0 \times 10^{-3}$ |
| CSML-100 | 3700 | $1.1 \times 10^6$ | $3.3 \times 10^{-3}$ |

Figure 11:
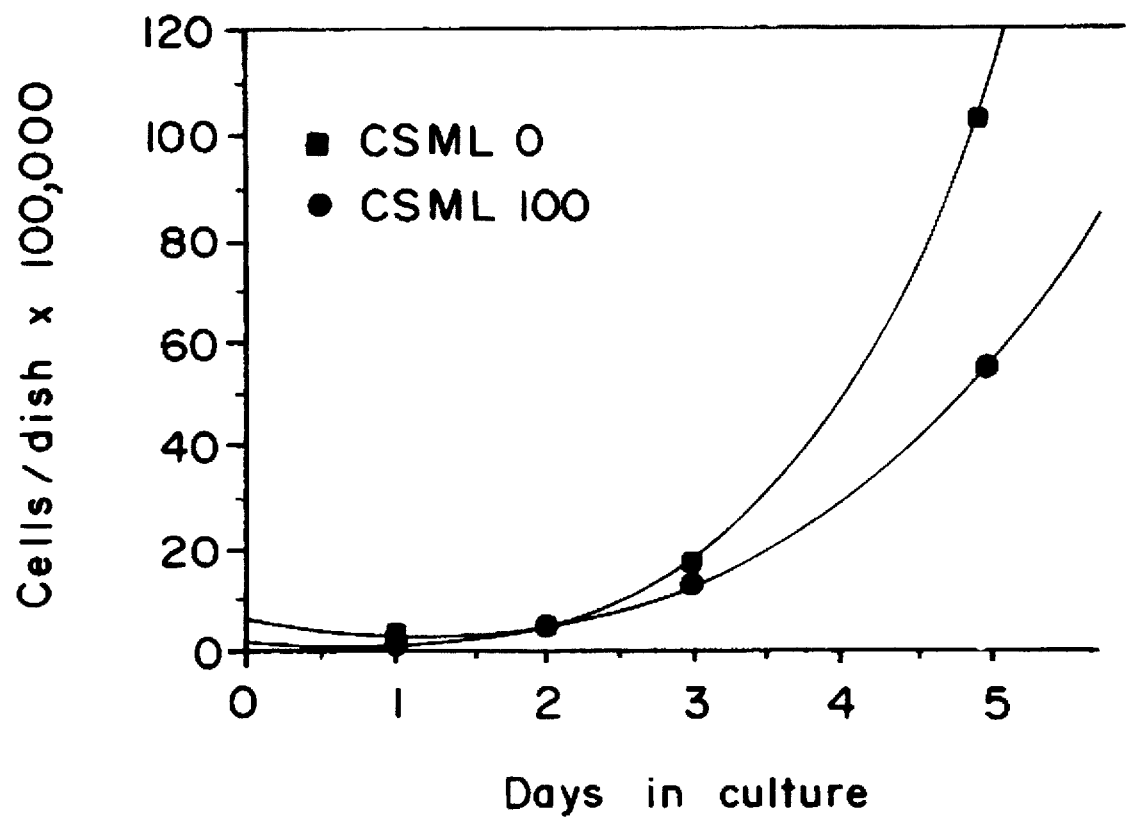
FIG. 11 depicts a growth curve of CSML-0 and CSML-100 cells over a five day period. Cell growth was measured daily by observing the number of cells per dish (ordinate). As illustrated, CSML-100 cells, which express high levels of mts-1, grow at a slower rate than CSML-0 cells which express little mts-1.

In particular, only $1.1 \times 10^6$ CSML-100 cells are observed per dish, whereas $1.6 \times 10^6$ CSML-0 cells are observed. Since $1 \times 10^6$ cells of both type were plated, the CSML-100 cell growth was only about one-sixth that of the CSML-0 cell growth. FIG. 11 further illustrates that the growth of CSML-100 cells from a 2-day to at least a 5-day period is less than that of CSML-0 cells.

EXAMPLE 15 mts-1 MRNA Can Be Detected by Hybridization of mts-1 Antisense Probes to Tissue Sections Methods Mouse embryonic trophoblast cells express mts-1. To illustrate the efficacy of mts-1 nucleic acid probes for detection of mts-1 mRNA in tissue sections, frozen sections of an 8 day mouse embryo were obtained. Sections were placed onto a standard microscope slide and fixed for 5 min. with 3% formaldehyde, 0.1M phosphate buffer, pH 7.2.

Sense and antisense mts-1 riboprobes were prepared by in vitro transcription from a pGEM-2-mts-1 vector containing the 3' untranslated region of mts-1 using $T_7$ and $T_3$ RNA polymerases according to the manufacturers direction. Transcription was with $^3H$-UTP (45 µG, Amersham).

Prior to hybridization, slides were acetylated with 0.25% (v/v) acetic anhydride in 0.1M ariethanolamine for 10 minutes at room temperature. The sections were rinsed in 2× SSC and dehydrated through an ethanol series (30%, 50%, 70%, 85%, 95%, 99%, 99%).

To the dried sections, 20 µl of hybridization solution (0.3M NaCl, 20 mM Tris pH 8, 1 mM EDTA, 50% formamide, 10% dextran sulfate, 1× Denhardt's, 500 µg/ml yeast RNA) containing ~$10^4$ cpm/||$l^3$H sense or antisense probe, preheated to 80° C., was applied and secured with a coverslip. The slides were immersed in mineral oil and incubated at 45° C. for ~12 hours. Excess mineral oil was removed from slides, and slides were washed through chloroform 3 times. Slides were next rinsed 3×5 in 4× SSC to remove coverslips. RNase digestion (20 µg/ml RNase A, 1U/ml RNase $T_1$) in 0.5M NaCl, 10mM Tris pH 8.0, 1 mM EDTA) was done for 30 minutes at 37° C. Slides were washed once in RNase buffer for 30 minutes, 37° C.; then in 4 liters 2× SSC for 30 minutes at room temperature; next in 0.1× SSC at 55° C. for 30 minutes; finally in 4 liters 0.1× SSC at room temperature for 30 minutes. Slides were dehydrated through an ethanol series containing 300 mM ammonium acetate. Once slides were dry, they were dipped in NTB-2 emulsion (Kodak) |diluted 1:1 with 600 mM ammonium acetate] and autoradiographed for 4 weeks. Slides were developed in D-19 2.5 minutes, fixed in 2% acetic acid 30 seconds, fixed for 5 minutes and rinsed in water for 30 minutes. Finally, sections were counter stained, cover slipped and photographed using dark-field illumination.

Results

Figure 12A:
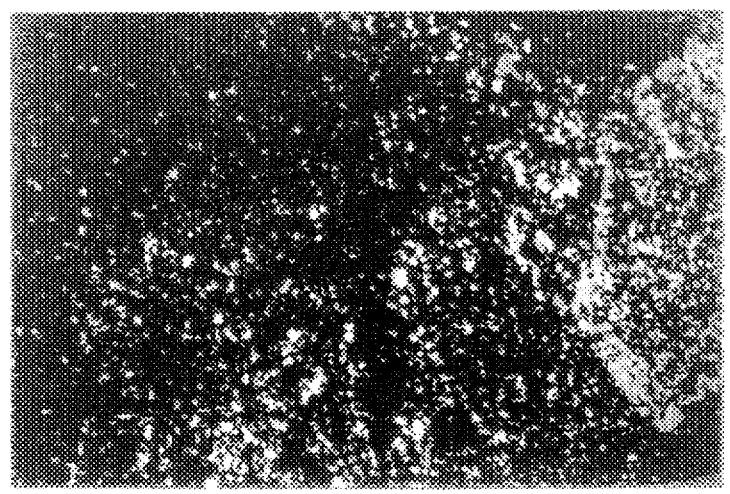
FIG. 12a depicts a photomicrograph of a section from an 8 day mouse embryo hybridized with a $^3$H-labelled mts-1 antisense probe. Signal is detected in the trophoblast cells.
Figure 12B:
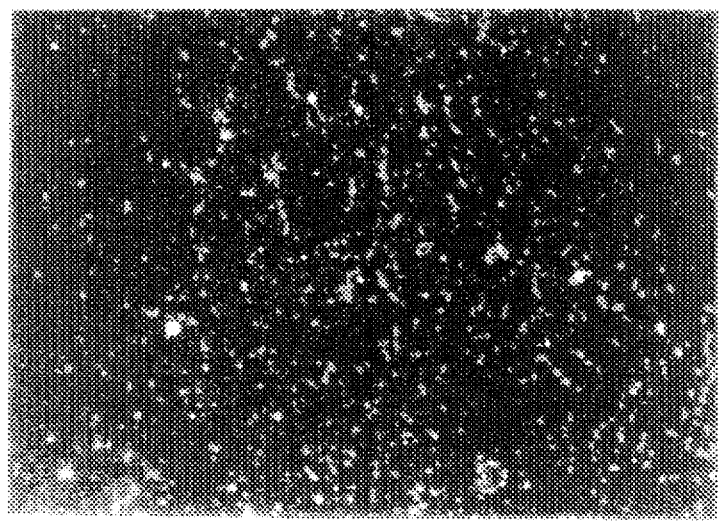
FIG. 12b depicts a photomicrograph of a section from an 8 day mouse embryo hybridized with a $^3$H-labelled mts-1 sense probe. No signal is detected.

Hybridized mts-1 probe was detected in mouse trophoblast cells only when the mts-1 probe was an antisense probe (FIG. 12a). The sense mts-1 probe gave rise to no signal (FIG. 12b). These data indicate that an antisense mts-1 probe can be used to detect mts-1 mRNA in tissue sections.

EXAMPLE 16

Chicken Anti-mts-1 Antibody Detects mts-1 Protein by Western Blot and Immunohistochemistry Methods The chicken anti-mts-1 antibody (α-mts-1) was prepared as described in Example 9.

Lysates of CSML-0 and CSML-100 cells were electrophoresed on 12% SDS-PAGE gels and transferred to polyvinyledene difluoride (PVDF) membranes for Western blot analysis. Membranes containing 3 µg purified mts-1 were incubated with anti-mts-1 antibody (1:2000) for 3 hours at room temperature and then with anti-chicken IgG-HRP at room temperature for 2 hours. Signal was detected with diaminobenzene (DAB).

To test the specificity of the α-mts-1 antibody, membranes containing CSML-100 proteins were probed with α-mts-1 in the presence and absence of 260 ng free recombinant mts-1 protein. Membranes containing 3 µg purified mts-1 were treated as above but upon addition of the primary antibody (α-mts-1) 13 µg of purified free mts-1 was added.

Frozen mouse spleens were sectioned and fixed onto glass slides. Sections were probed with a 1:1000 dilution of α-mts-1 in PBA according to the method of Harlow et al. To test the specificity of the α-mts-1 antibody, 130 ng free mts-1 protein was applied to one series of slides along with the diluted α-mts-1 antibody.

The α-mts-1 antibody was deemed specific for mts-1 protein when free mts-1 effectively eliminated binding of α-mts-1 to mts-1 Western blots or mouse spleen sections.

Results

FIG. 13 depicts a Western blot of CSML-0 (Lane 1) and CSML-100 (Lanes 2 and 3) cell lysates. Lanes 1 and 2 were probed with α-mts-1 antibody without added free mts-1 protein. As illustrated, a 10–12 Kd mts-1 protein is expressed in CSML-100 cells (Lane 2) but not in CSML-0 cells (Lane 1). Moreover, 260 ng free mts-1 protein effectively eliminated antibody binding to the CSML-100 cell lysate in Lane 3. Therefore, the α-mts-1 antibody is highly specific for mts-1 protein.

Figure 14B:
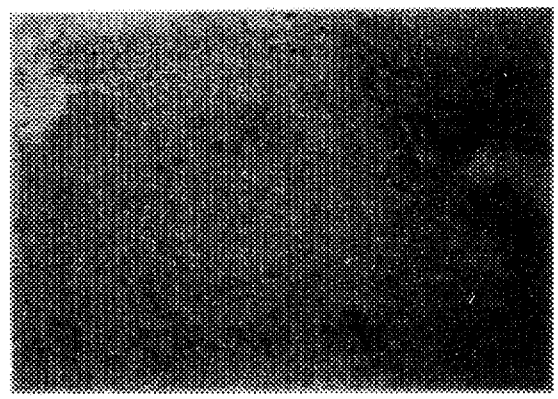
FIG. 14b depicts a frozen mouse spleen section probed with the α-mts-1 antibody in the presence of free mts-1 protein. Rabbit anti-chicken IgG-HRP was used for detection of the mts-1 antigen-antigen complex (dark spots). As illustrated, little or no mts-1 protein is detected when free mts-1 protein is present to compete for binding to α-mts-1 (compare to FIG. 14a). Therefore, the α-mts-1 antibody is highly specific for mts-1 protein.

Similarly, mts-1 protein is detected in frozen mouse spleen sections (FIG. 14a) and α-mts-1 antibody binding on such tissue sections is eliminated when free mts-1 protein is applied to the sections with the antibody (FIG. 14b).

Accordingly, mts-1 protein can readily be detected on Western blots and on tissue sections using the α-mts-1 antibody.

EXAMPLE 17

Figure 15A:
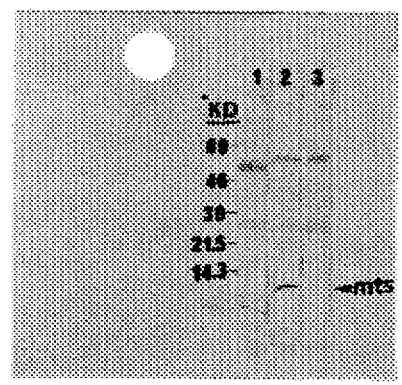
FIG. 15a illustrates that mts-1 protein can be detected only in serum from mice injected with CSML-100 cells. This figure depicts a western blot of serum taken from non-injected mice (Lane 3), mice injected with 1×10$^5$ CSML-0 cells (Lane 1) and mice injected with 1×10$^5$ CSML-100 cells (Lane 2). After reaction with the α-mts-1 antibody a 10–12 kd mts-1 protein is detected only in the serum from mice injected with CSML-100 cells. The higher molecular weight bands merely cross-react with the anti-mts-1 antibody used and were not mts-1 proteins.
Figure 15B:
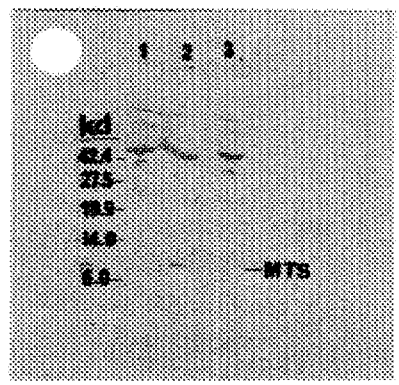
FIG. 15b similarly illustrates that mts-1 protein can be detected only in serum from mice injected with CSML-100 cells. This figure depicts a western blot of serum taken from non-injected mice (Lane 3), mice injected with 1×10$^6$ CSML-0 cells (Lane 1) and mice injected with 1×10$^6$ CSML-100 cells (Lane 2). After reaction with the α-mts-1 antibody a 10–12 kd mts-1 protein is detected only in the serum from mice injected with CSML-100 cells. As described, the higher molecular weight bands merely cross-react with the anti-mts-1 antibody used and were not mts-1.

Low Molecular Weight mts-1 Protein is Found Only in Serum From Animals with Metastatic Cancer Methods Mouse Studies:

CSML-0 and CSML-100 cells were injected intravenously into the tail veins of A/J mice at $1\times10^5$ cells per mouse (FIG. 15a, Lane 2) or $1\times10^6$ cells per mouse (FIG. 15b, Lane 2). After three weeks the mice were sacrificed, their lungs examined for the presence of metastasis, and their blood drawn. Blood was allowed to clot at room temperature for one hour and was then microfuged to isolate sera. The sera samples were loaded at 100 µg per lane on a 13% SDS-PAGE gel (FIG. 15a) or a 13% Tris-Tricine gel (FIG. 15b). The proteins were then transferred to PVDF membranes and probed with a 1:1000 dilution of α-mts-1 antibody and a horse-radish peroxidase conjugated secondary antibody.

mts-1 is expressed in T lymphocytes and activated macrophages. To test whether the detected mts-1 protein resulted from lysis of normal blood cells including T lymphocytes and macrophages, whole mouse blood was lysed and probed with α-mts-1 antibody in a western blot analysis. Whole blood was taken from a normal mouse, lysed in a triton-X100 solution and electrophoresed on a 13% Tris-Tricine gel. A PVDF membrane blot of the gel was prepared and probed as above.

To determine whether the presence of mts-1 in sera is simply due to a chronic immune response which might increase the number of T lymphocytes and activated macrophages, mice were injected with salmonella LPS over an extended time period to induce a chronic immune response. Sera were drawn and western analysis was performed as described above.

Human Studies

Serum samples were obtained from normal women and patients with breast carcinomas or advanced malignant lymphomas. 150 µg of each serum sample was run on a 12% SDS-PAGE gel. The proteins were transferred to PVDF membranes and the membranes were probed with a 1:1000 dilution of α-mts-1 and then with a 1:1000 dilution of the secondary antibody (rabbit anti-chicken IgG-HRP). The reaction was developed with a DAB solution.

Results

Mouse Studies

Three weeks after intravenous injection, the mice receiving CSML-100 looked very sick and had breathing difficulties. Western analysis of sera from injected and non-injected animals indicated that only those mice receiving CSML-100 cells had a 10–12 Kd mts-1 protein (FIGS. 15a and 15b, Lane 2). Injection of as little as $10^5$ CSML-100 cells three weeks prior to western analysis produced a positive serum response. The lungs of those mice injected with either $10^5$ or $10^6$ CSML-100 cells had extensive metastasis.

The α-mts-1 antibody detected a high molecular weight band in all samples on the western blot. However, addition of free mts-1 protein to the Western blot when incubating with the α-mts-1 antibody did not eliminate the signal from the high molecular weight band. Only the lower molecular weight band found in CSML-100 injected mice was eliminated by competing free mts-1 protein. Therefore, only the lower molecular weight band is mts-1 protein. The higher molecular weight band may be an abundant serum protein which cross-reacts with the α-mts-1 polyclonal antibody.

Figure 15C:
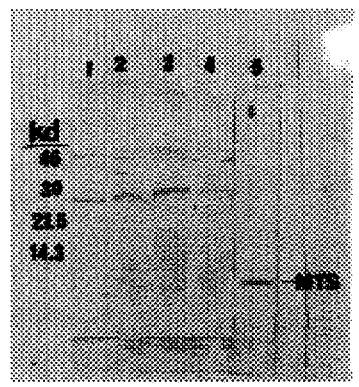
FIG. 15c depicts a western blot of lysed whole blood from mice probed with the α-mts-1 antibody. Lanes 1–4 were loaded with 5, 10, 20 and 25 μl lysed whole blood, respectively. Lane 5 was loaded with CSML-100 cell lysate as a positive control. This blot illustrates that mts-1 protein in serum is not simply due to lysis of lymphocyte or blood cells.

FIG. 15c illustrates that the mts-1 protein detected in serum is not a normal component of whole blood and is not a result of a chronic immune response. The mts-1 protein is not detected in lysed whole blood cells (FIG. 15c, Lanes 1–4 containing 5, 10, 20 and 25 µl lysed whole blood). However, mts-1 was detected in similarly treated CSML-100 cells which were provided as a positive control (FIG. 15c, Lane 5).

Figure 15D:
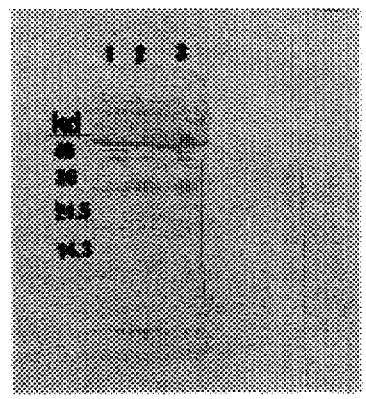
FIG. 15d depicts a western blot of increasing amounts of serum from mice injected with salmonella lipopolysaccharide (LPS) to induce a chronic immune response. The blot was probed with the α-mts-1 antibody to reveal any detectable mts-1 protein. Lanes 1–3 were loaded with 75, 100 or 150 μg serum, respectively. This blot illustrates that mts-1 protein in serum is not derived from activated macrophages generated by a chronic immune response.

FIG. 15d illustrates that the mts-1 protein detected in sera of metastatic cancer patients is not due to a chronic immune response induced by salmonella LPS over an extended period of time. The mts-1 protein could not be detected in the 75 µg, 100 µg or 150 µg of sera from chronically immunologically stimulated mice (FIG. 15d, Lanes 1–3).

Accordingly, a 10–12 Kd mts-1 protein can be detected in sera of mice with metastatic cancer. No mts-1 protein is detected in the serum of control mice.

Human Studies

Figure 16:
FIG. 16 depicts a western blot of sera from patients with non-metastatic and metastatic cancers probed with the α-mts-1 antibody to reveal any detectable mts-1 protein. A 27 kd mts-1 protein is detected only in patients known to have metastatic cancer. Sera were taken from patients with non-metastatic breast cancer (Lane 1), with non-metastatic lymphomas (Lanes 2 and 4), with metastatic lymphomas (Lanes 5 and 7) and with metastatic breast cancer (Lane 6). Lane 3 contains normal serum as a negative control. The higher molecular weight proteins merely cross-react with the α-mts-1 antibody and do not represent mts-1 protein products.

FIG. 16 illustrates that mts-1 protein can be detected only in sera from patients known to have metastatic cancer. An approximate 27 Kd mts-1 protein could be detected in serum from a patient with metastatic breast cancer (FIG. 16, Lane 6) and in two patients with metastatic lymphomas (FIG. 16, Lanes 5 and 7).

However, no such 27 Kd mts-1 protein was detected in serum from a normal patient (FIG. 16, Lane 3) or in serum from patients with non-metastatic breast cancer (FIG. 16, Lane 1) or non-metastatic lymphomas (FIG. 16, Lanes 2 and 4).

The higher molecular weight band apparent in FIGS. 16a–d is not mts-1 protein. In particular, when the Western blot is probed with α-mts-1 antibody in the presence of free mts-1 protein, only the 27 Kd protein band disappears. Free mts-1 protein does not eliminate the high molecular weight signal. Therefore, the α-mts-1 polyclonal antibody may cross-react with an abundant serum protein. Such cross-reactivity can be eliminated by, for example, using an antibody directed against human mts-1 protein (α-mts-1 is directed against mouse mts-1 protein) or by employing highly specific monoclonal antibodies prepared as described in Example 10.

Accordingly, mts-1 protein is detectable only in sera from patients with metastatic cancer. The mts-1 protein cannot be detected in the serum of normal patients or in the serum of patients with non-metastatic cancer. Antibodies directed against mts-1 protein can therefore be used in a simple serum immunoassay to diagnose and detect metastatic cancer in patients.

What is claimed is:

1. An isolated nucleic acid encoding a human mts-1 protein.

2. The isolated nucleic acid of claim 1 wherein said nucleic acid is genomic DNA, cDNA or RNA.

3. An isolated nucleic acid encoding a human mts-1 protein having the nucleotide sequence set forth in SEQ. ID. NO:1.

4. An isolated nucleic acid encoding a human mts-1 having the nucleotide sequence set forth in SEQ. ID. NO:3.

5. A host cell comprising the nucleic acid of any one of claims 1, 2, 3, 4 which host cell permits expression of a protein encoded by said nucleic acid.

6. A host cell according to claim 5 wherein said cell is yeast.

7. A host cell according to claim 5 wherein said cell is a bacterium.

8. A host cell according to claim 5 wherein said cell is a mammalian cell.

9. A host cell according to claim 5 wherein said cell is an insect cell.

10. A mammalian cell line which is transformed with a gene which encodes human mit-1 protein.

11. A cell line expressing the mts-1 protein having SEQ ID NO:2 or an antigenic fragment thereof, wherein said antigenic fragment generates antibodies human mts-1 protein, and comprises at least four contiguous amino acids of SEQ ID NO:2.

12. A cell line according to claim 11 wherein the mts-1 protein or antigenic fragment thereof is detectable with anti-mts-1 antibodies.

13. An isolated nucleic acid encoding an mts-1 protein fragment having the amino acid sequence of SEQ ID NO:4.

14. An isolated nucleic acid encoding an mts-1 protein fragment having the amino acid sequence of SEQ ID NO:5.

15. An isolated nucleic acid encoding an mts-1 protein fragment having the amino acid sequence of SEQ ID NO:6.

16. An isolated nucleic acid encoding an mts-1 protein fragment having the amino acid sequence of SEQ ID NO:7.

17. An isolated nucleic acid encoding a human mts-1 protein fragment having the amino acid sequence of SEQ ID NO:2.

18. An isolated nucleic acid encoding an antigenic fragment of human mts-1 protein which fragment generates antibodies human mts-1 protein, and comprises at least 4 contiguous amino acids of SEQ ID NO:2.

19. The isolated nucleic acid of claim 18 wherein said nucleic acid is genomic DNA, cDNA or RNA.

20. A replicable expression vector comprising the nucleic acid of claim 1 or 18 operably linked to a nucleotide sequence capable of effecting expression of a polypeptide encoded by said nucleic acid.

* * * * *

UNITED STATES PATENT AND TRADEMARK OFFICE
CERTIFICATE OF CORRECTION

PATENT NO. : 5,798,257
DATED : August 25, 1998
INVENTOR(S) : Sayeeda Zain et al.

It is certified that error appears in the above-identified patent and that said Letters Patent is hereby corrected as shown below:

Title page,
Item [56], "PUBLICATIONS",
Line 21, "(14)" should read -- (4) --

Column 1,
Line 4, insert the following: -- This invention was made with Government support under CA-36432 awarded by the National Institutes of Health. The Government has certain rights in the invention. --

Column 25,
Line 61, "gents" should read -- agents --

Column 27,
Lines 41 & 55, "mts" should read -- mts-1 --

Column 29,
Line 53, "abut" should read -- about --

Column 36,
Line 4, "cpm/ ‖1³" should read -- $cpm/\mu l^3$ --

Column 43, claim 4,
Line 40, "mts-1" should read -- mts-1 protein --

Column 43, claim 10,
Line 53, "mit-1" should read -- mts-1 --

UNITED STATES PATENT AND TRADEMARK OFFICE
CERTIFICATE OF CORRECTION

PATENT NO. : 5,798,257
DATED : August 25, 1998
INVENTOR(S) : Sayeeda Zain et al.

It is certified that error appears in the above-identified patent and that said Letters Patent is hereby corrected as shown below:

Column 43, claim 11,
Line 56, after "antibodies" insert -- which detect --

Signed and Sealed this

Fifth Day of March, 2002

Attest:

Attesting Officer

JAMES E. ROGAN
Director of the United States Patent and Trademark Office